(12) United States Patent
Goldberger et al.

(10) Patent No.: US 10,074,814 B2
(45) Date of Patent: Sep. 11, 2018

(54) GERMANANE ANALOGS AND OPTOELECTRONIC DEVICES USING THE SAME

(71) Applicant: OHIO STATE INNOVATION FOUNDATION, Columbus, OH (US)

(72) Inventors: Joshua Goldberger, Columbus, OH (US); Shishi Jiang, Columbus, OH (US); Elisabeth Bianco, Wadsworth, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 1138 days.

(21) Appl. No.: 14/244,572

(22) Filed: Apr. 3, 2014

(65) Prior Publication Data

US 2017/0200906 A1 Jul. 13, 2017

Related U.S. Application Data

(60) Provisional application No. 61/814,412, filed on Apr. 22, 2013, provisional application No. 61/822,065, filed on May 10, 2013.

(51) Int. Cl.
*C01G 17/00* (2006.01)
*H01L 51/00* (2006.01)
(Continued)

(52) U.S. Cl.
CPC ............ *H01L 51/0077* (2013.01); *C01B 6/06* (2013.01); *C07F 7/2212* (2013.01); *C07F 7/30* (2013.01); *H01L 29/0665* (2013.01); *H01L 29/24* (2013.01); *H01L 31/032* (2013.01); *H01L 31/035209* (2013.01); *H01L 33/04* (2013.01); *H01L 33/26* (2013.01); *B82Y 20/00* (2013.01);
(Continued)

(58) Field of Classification Search
CPC . H01L 51/0077; H01L 29/0665; H01L 29/24; H01L 31/032; H01L 31/035209; H01L 33/04; H01L 33/26; H01L 51/0558; H01L 51/42; H01L 51/50; C01B 6/06; C07F 7/2212; C07F 7/30; B82Y 20/00; B82Y 30/00; B82Y 40/00; Y10S 977/758; Y10S 977/788; Y10S 977/896; Y10S 977/933; Y10S 977/95
See application file for complete search history.

(56) References Cited

U.S. PATENT DOCUMENTS

2003/0151117 A1* 8/2003 Vogg .................... H01L 51/0032
257/616

FOREIGN PATENT DOCUMENTS

JP 2007254593 A * 10/2007
JP 2008069301 3/2008
(Continued)

OTHER PUBLICATIONS

Machine translation of JP 2007-254593A, Translated Sep. 27, 2017. (Year: 2007).*
(Continued)

*Primary Examiner* — David R Sample
*Assistant Examiner* — Elizabeth A Collister
(74) *Attorney, Agent, or Firm* — Michael Best & Friedrich LLP

(57) ABSTRACT

The present invention provides novel two-dimensional van der Waals materials and stacks of those materials. Also provided are methods of making and using such materials.

19 Claims, 31 Drawing Sheets

(51) Int. Cl.
| | |
|---|---|
| *H01L 29/06* | (2006.01) |
| *H01L 31/0352* | (2006.01) |
| *H01L 33/04* | (2010.01) |
| *H01L 33/26* | (2010.01) |
| *H01L 31/032* | (2006.01) |
| *H01L 29/24* | (2006.01) |
| *C07F 7/30* | (2006.01) |
| *C01B 6/06* | (2006.01) |
| *C07F 7/22* | (2006.01) |
| *B82Y 40/00* | (2011.01) |
| *B82Y 30/00* | (2011.01) |
| *B82Y 20/00* | (2011.01) |
| *H01L 51/05* | (2006.01) |
| *H01L 51/42* | (2006.01) |
| *H01L 51/50* | (2006.01) |
| *C01G 19/00* | (2006.01) |

(52) U.S. Cl.
CPC .............. *B82Y 30/00* (2013.01); *B82Y 40/00* (2013.01); *C01G 17/00* (2013.01); *C01G 19/00* (2013.01); *H01L 51/0558* (2013.01); *H01L 51/42* (2013.01); *H01L 51/50* (2013.01); *Y10S 977/758* (2013.01); *Y10S 977/788* (2013.01); *Y10S 977/896* (2013.01); *Y10S 977/933* (2013.01); *Y10S 977/95* (2013.01)

(56) References Cited

FOREIGN PATENT DOCUMENTS

| | | |
|---|---|---|
| JP | 2010132640 | 6/2010 |
| JP | 2010215895 | 9/2010 |
| JP | 2011020884 | 2/2011 |
| WO | 2006/009073 | 1/2006 |

OTHER PUBLICATIONS

Blanco et al., "Stability and Exfoliation of Germanane: A Germanium Graphane Analog," ACS Nano, 2013, 7(5):4414-4421.

Jiang et al., "Improving the stability and optical properties of germanane via one-step covalent methyl-termination," Nature Communications, 2014, 5:3389, 6 pages.

Vogg et al., "Polygermyne—A Prototype System for Layered Germanium Polymers," Advanced Materials, 2000, vol. 12, Issue 17, pp. 1278-1281.

* cited by examiner

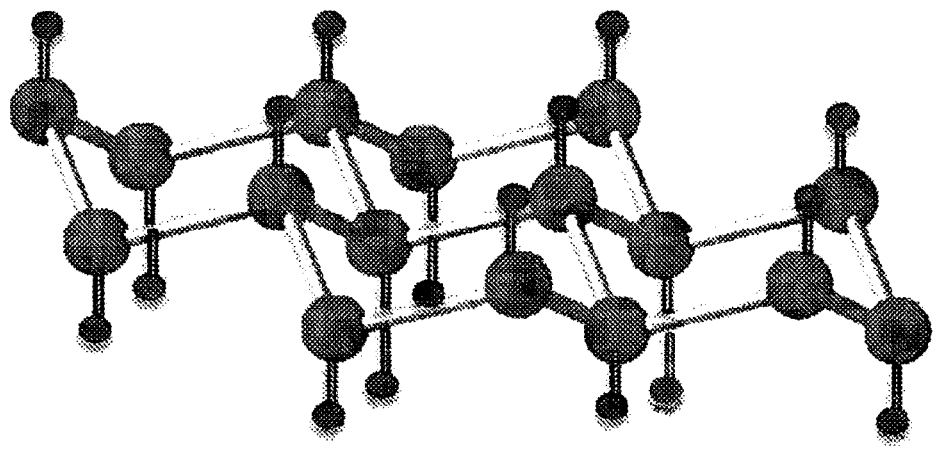
GRAPHANE
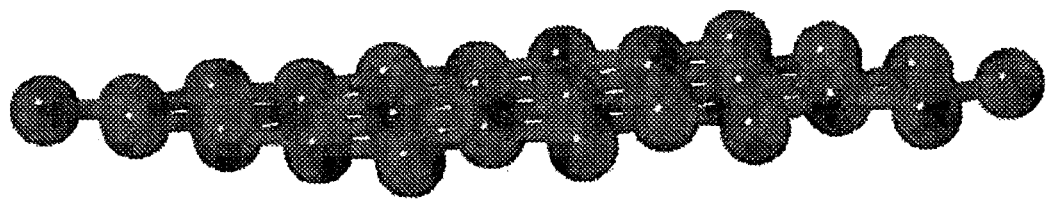
GRAPHENE
FIG. 1

| GeR | precursor RI |
|---|---|
| GeC$_n$H$_{2n+1}$ | C$_n$H$_{2n+1}$I (n=1-10, 12, 16, 18) linear chain |
| GeCH(CH$_3$)$_2$ | (CH$_3$)$_2$CHI |
| GeCH$_2$CH(CH$_3$)$_2$ | (CH$_3$)$_2$CHCH$_2$I |
| GeCH$_2$CH$_2$CH(CH$_3$)$_2$ | (CH$_3$)$_2$CHCH$_2$CH$_2$I |
| GeCH$_2$C(CH$_3$)$_3$ | (CH$_3$)$_3$CCH$_2$I |
| GeCH$_2$CH(CH$_3$)(CH$_2$)$_3$CH$_3$ | CH$_3$(CH$_2$)$_3$CH(CH$_3$)CH$_2$I |
| GeCH$_2$C$_3$H$_5$ | (Iodomethyl)cyclopropane |
| GeC$_n$F$_{2n+1}$ | C$_n$F$_{2n+1}$I (n=1-4, 8, 12) linear chain |
| GeCH$_2$CH$_2$C$_n$F$_{2n+1}$ | ICH$_2$CH$_2$C$_n$F$_{2n+1}$ (n=2, 4, 6, 8, 10) linear chain |
| GeCH$_2$CF$_3$ | CF$_3$CH$_2$I |
| Ge(CH$_2$)$_3$CF$_2$(CF$_2$)$_6$CF$_3$ | CF$_3$(CF$_2$)$_6$CF$_2$(CH$_2$)$_2$CH$_2$I |
| GeCF$_2$C$_6$F$_5$ | C$_6$F$_5$CF$_2$I (Heptafluorobenzyl iodide) |
| GeCH$_2$CH=CH$_2$ | CH$_2$=CHCH$_2$I |
| GeCH$_2$C(CH$_3$)=CH$_2$ | CH$_2$=C(CH$_3$)CH$_2$I |
| GeCH$_2$I or GeCH$_2$Ge | CH$_2$I$_2$ |
| GeCH$_2$CH$_2$I or GeCH$_2$CH$_2$I | ICH$_2$CH$_2$I |
| GeCHICH$_3$ GeCH(CH$_3$)Ge | CH$_3$CHI$_2$ |
| | |
| GeR | precursor RBr |
| GeCH$_2$CCH | HCCCH$_2$Br |
| GeCH=CH$_2$ | CH$_2$=CHBr |
| GeCH$_2$CH=CHCH$_3$ | CH$_3$CH=CHCH$_2$Br |
| GeCH$_2$CH=C(CH$_3$)$_2$ | (CH$_3$)$_2$C=CHCH$_2$Br |
| Ge(CH$_2$)$_8$CH=CH(CH$_2$)$_7$CH$_3$ | CH$_3$(CH$_2$)$_7$CH=CH(CH$_2$)$_7$Br |
| GeCH$_2$Ph | PhCH$_2$Br (Benzyl bromide) |

FIG. 2

GERMANANE ANALOGS AND OPTOELECTRONIC DEVICES USING THE SAME

CROSS-REFERENCE TO RELATED APPLICATIONS

This application claims the benefit of U.S. Provisional Application No. 61/814,412 filed Apr. 22, 2013, and U.S. Provisional Application No. 61/822,065, filed May 10, 2013; both of which are fully incorporated by reference herein.

STATEMENT REGARDING FEDERALLY SPONSORED RESEARCH

This invention was made with government support under grant/contract no. NSF/DMR-1201953 awarded by NSF and grant/contract no. W911-NF-12-1-0481 awarded by DARPA—ARMY/ARO. The government has certain rights in the invention.

BACKGROUND

Two-dimensional van der Waals materials have shown great promise for a variety of electronic, optoelectronic, sensing and energy conversion applications. New materials are needed for such applications as well as new ways of making such two-dimensional van der Waals materials.

SUMMARY

In an embodiment, the invention provides a two-dimensional layer comprising M-R, wherein M is selected from the group consisting of Ge, and Sn; and wherein R is $C_{1-18}$ alkyl or OH.

In an embodiment, the invention provides a stack comprising the two-dimensional layer of M-R.

In an embodiment, the invention provides an alloy comprising $Ge_{1-x}Sn_xR^3$, wherein $R^3$ is H, OH or $C_{1-18}$ alkyl and x is about 0 to about 1; wherein $R^3$ is not H if x is zero.

In an embodiment, the invention provides an alloy comprising $Ge_{1-x}Si_xR^6$, wherein $R^6$ is OH or $C_{1-18}$ alkyl and x is about 0 to about 1.

In an embodiment, the invention provides a light-emitting device comprising a two-dimensional layer comprising M-R, a stack of such layers, or an alloy of $Ge_{1-x}Sn_xR^3$ or $Ge_{1-x}Si_xR^6$.

In an embodiment, the invention provides a light-absorbing device comprising a two-dimensional layer comprising M-R, a stack of such layers, or an alloy of $Ge_{1-x}Sn_xR^3$ or $Ge_{1-x}Si_xR^6$.

In an embodiment, the invention provides a transistor comprising a two-dimensional layer comprising M-R, a stack of such layers, or an alloy of $Ge_{1-x}Sn_xR^3$ or $Ge_{1-x}Si_xR^6$.

In an embodiment, the invention provides a method of synthesizing M-R comprising reacting $A-M_2$ with R—X to form M-R.

In an embodiment, the invention provides a method of synthesizing $Ge_{1-x}Sn_xR^3$ comprising reacting $AGe_{2-y}Sn_y$ with $R^3$—X to form $Ge_{1-x}Sn_xR^3$.

In an embodiment, the invention provides a method of synthesizing $Ge_{1-x}Si_xR^6$ comprising reacting $CaGe_{2-y}Si_y$ with $R^6$—X to form $Ge_{1-x}Si_xR^6$.

Other aspects of the invention will become apparent by consideration of the detailed description and accompanying drawings.

BRIEF DESCRIPTION OF THE DRAWINGS

FIG. 1 is a depiction of graphane vs. graphene.

FIG. 2 is a list of useful organo halide reagents and there resulting organogermanane.

DETAILED DESCRIPTION

Figure 3:
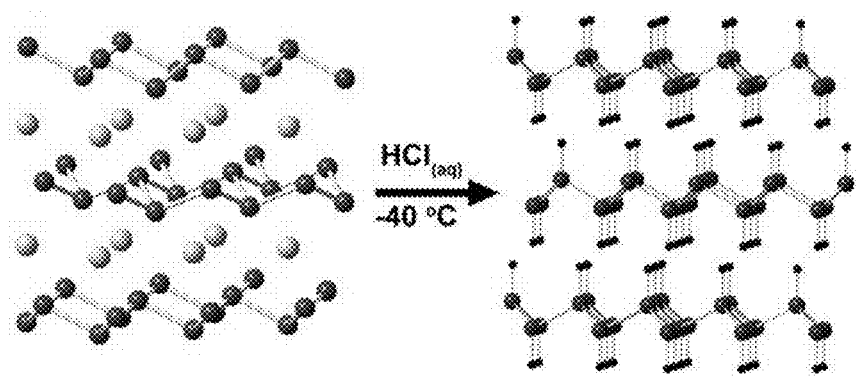
FIG. 3 is a schematic illustration of the topotactic deintercalation of $CaGe_2$ to GeH.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

There has been widespread interest in the exploration of the unique properties and applications of single and few-layer thick sheets of layered van der Waals materials such as graphene, or the layered transition metal dichalcogenides. This work has shown the significant role of the immediate environment on the properties and reactivity of these van der Waals layers. Therefore, the properties of single atom thick materials may be manipulated by covalent termination with various substituents. In contrast to the negligible role the surface-binding ligand plays in nanoscale materials, terminating the surface of single-atom thick materials with different ligands may allow for the broad tuning of properties including band gap, band alignment, thermal stability, carrier mobility, and spin-dependent interactions.

Unfortunately, most of the two-dimensional materials studied to date are comprised of neutral van der Waals layers that lack the possibility of covalent functionalization. Although the functionalization of graphene with organic components, hydrogen atoms or even halogens have been achieved, these modifications completely disrupt the excellent electronic mobility of the Fermi-Dirac state, to produce 3-5 eV band gap semiconductors.

To bypass the potential air reactive intermediates and create new organic-terminated materials, new single-step synthetic methods that can directly convert a precursor crystalline solid-state crystal into a crystalline, exfoliatable, organic-terminated van der Waals solid in nonaqueous solvents is required.

Thus, the invention provides, among other things, a two-dimensional van der Waals material, such as an organogermanane or an organostannane. The invention also provides a stack of two-dimensional layers of the two-dimensional van der Waals material. The invention further provides a method of synthesizing the two-dimensional van der Waals material and methods of using such materials.

Definitions

As used herein, the term "alkyl" refers to a branched, unbranched, or cyclic hydrocarbon (a "cycloalkyl") having, for example, from 1 to 18 carbon atoms, and often 1 to 12, 1 to 10, 1 to 8, 1 to 7, 1 to 6, 1 to 5 or 1 to 4 carbon atoms. Examples include, but are not limited to, methyl, ethyl, 1-propyl, 2-propyl, cyclopropyl, 1-butyl, 2-methyl-1-propyl, 2-butyl, 2-methyl-2-propyl (t-butyl), cyclobutyl, 1-pentyl, 2-pentyl, 3-pentyl, 2-methyl-2-butyl, 3-methyl-2-butyl, 3-methyl-1-butyl, 2-methyl-1-butyl, cyclopentyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, cyclohexyl, heptyl, octyl, decyl, dodecyl, and the like. The alkyl can be unsubstituted or substituted. The alkyl can also be optionally partially or fully unsaturated.

As used herein, "aryl" refers to an aromatic hydrocarbon group derived from the removal of one hydrogen atom from a single carbon atom of a parent aromatic ring system. The radical can be at a saturated or unsaturated carbon atom of the parent ring system. The aryl group can have from 6 to 30 carbon atoms, for example from 6 to 20 carbon atoms or 6 to 14 carbon atoms. For example, the aryl group may be a C6, C10, C12, C13 or C14 aryl group. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described above for alkyl groups.

As used herein, "halo" or "halogen" refers to fluorine, chlorine, bromine or iodine.

It is specifically understood that any numerical value recited herein includes all values from the lower value to the upper value, i.e., all possible combinations of numerical values between the lowest value and the highest value enumerated are to be considered to be expressly stated in this application. For example, if a concentration range or a beneficial effect range is stated as 1% to 50%, it is intended that values such as 2% to 40%, 10% to 30%, or 1% to 3%, etc., are expressly enumerated in this specification. These are only examples of what is specifically intended.

Also, it is to be understood that the phraseology and terminology used herein is for the purpose of description and should not be regarded as limiting. The use of "comprising," "including," "having," and variations thereof herein is meant to encompass the items listed thereafter and equivalents thereof as well as additional items.

Compounds and Compositions

In embodiments, the present invention provides a two-dimensional layer of M-R, wherein M is selected from the group consisting of Sn and Ge; and R is a $C_{1-18}$ alkyl or OH. In embodiments, M is Ge. The notation "M-R" or "germanane" or "GeR" or "stannane" or "Sn—R" is used herein to denote a structure comprising a two-dimensional sp-3 bonded Ge or Sn backbone with —R terminations.

In embodiments, R can be substituted with one or more substituents. Suitable substituents included halo and aryl, such as F, I, and phenyl. In embodiments, R is a perfluoro moiety. In embodiments, R is —$(CH_2)_nCH_3$ or —$(CF_2)_nCF_3$, wherein n is 1-17. In embodiments, R is —$CH_2CH_2(CF_2)_mCF_3$, wherein m is 1-10. In embodiments, R is —$CH_3$, —$CH(CH_3)_2$, —$CH_2CH(CH_3)_2$, —$CH_2CH_2CH(CH_3)_2$, —$CH_2C(CH_3)_3$, —$CH_2C_3H_5$, —$CH_2CH(CH_3)(CH_2)_3CH_3$, —$CH_2CF_3$, —$(CH_2)_3CF_2(CF_2)_6CF_3$, —$CH_2C_6H_5$, —$CF_2C_6F_5$, —$CH_2CH=CH_2$, —$CH_2C(CH_3)=CH_2$, —$CH_2I$, —$CH_2CH_2I$, $CHICH_3$, —$CH_2CCH$, —$CH=CH_2$, —$CH_2CH=CHCH_3$, —$CH_2CH=C(CH_3)_2$, or —$(CH_2)_8CH=CH(CH_2)_7CH_3$.

In embodiments, the present invention provides a stack of two-dimensional layers of M-R, wherein M and R are as described above. In embodiments, the stack may be more than about 1.2 nanometers thick or more than about 20 micrometers thick or more than about 30 micrometers thick. In embodiments, the stack may be less than about 100 micrometers thick or less than about 30 micrometers thick or less than about 20 micrometers thick. In embodiments, the stack may be about 1.2 nanometers to about 100 micrometers thick or about 1.2 nanometers to about 30 micrometers thick or about 1.2 nanometers to about 20 micrometers thick or about 20 micrometers to about 100 micrometers thick.

In embodiments, the present invention also provides an alloy comprising $Ge_{1-x}Sn_xR^3$, wherein x is about 0 to about 1; and $R^3$ is at least one of $C_{1-18}$ alkyl, H or OH; wherein $R^3$ can be H if x is greater than zero. In embodiments, the alloy is $Ge_{1-x}R^1Sn_xR^2$, wherein x is about 0 to about 1; and $R^1$ and $R^2$ are independently selected from H, $C_{1-18}$ alkyl and —OH and may be the same or different; wherein $R^1$ is not H if x is zero.

In embodiments, x is about 0.01, about 0.04, about 0.07, about 0.09, about 0.1, about 0.2, about 0.4, about 0.6, about 0.7, or about 0.8. In embodiments, x is about 0.01 to about 0.8 or about 0.01 to about 0.1 or about 0.1 to about 0.8 or about 0.2 to about 0.6. In embodiments, x is more than about 0 or more than about 0.01 or more than about 0.04 or more than about 0.07 or more than about 0.09 or more than about 0.1 or more than about 0.2 or more than about 0.4 or more than about 0.6 or more than about 0.7 or more than about 0.8. In embodiments, x is less than about 1 or less than about 0.8 or less than about 0.7 or less than about 0.6 or less than about 0.4 or less than about 0.2 or less than about 0.1 or less than about 0.09 or less than about 0.07 or less than about 0.04.

In embodiments, the present invention also provides an alloy comprising $Ge_{1-x}Si_xR^6$, wherein x is about 0 to about 1; and $R^6$ is at least one of $C_{1-18}$ alkyl or OH. In embodiments, the alloy is $Ge_{1-x}R^4Si_xR^5$, wherein x is about 0 to about 1; and $R^4$ and $R^5$ are independently selected from $C_{1-18}$ alkyl and —OH and may be the same or different.

In embodiments, x is about 0.01, about 0.04, about 0.07, about 0.09, about 0.1, about 0.2, about 0.4, about 0.6, about 0.7, or about 0.8. In embodiments, x is about 0.01 to about 0.8 or about 0.01 to about 0.1 or about 0.1 to about 0.8 or about 0.2 to about 0.6. In embodiments, x is more than about 0 or more than about 0.01 or more than about 0.04 or more than about 0.07 or more than about 0.09 or more than about 0.1 or more than about 0.2 or more than about 0.4 or more than about 0.6 or more than about 0.7 or more than about 0.8. In embodiments, x is less than about 1 or less than about 0.8 or less than about 0.7 or less than about 0.6 or less than about 0.4 or less than about 0.2 or less than about 0.1 or less than about 0.09 or less than about 0.07 or less than about 0.04.

Two-dimensional van der Waals materials according to the present invention may be direct band gap semiconductors. In embodiments, a multi-layer material comprising the two-dimensional van der Waals materials of the present invention is a direct band gap semiconductor. For example, a 50-layer thick stack may be a direct band gap semiconductor.

In embodiments, two-dimensional van der Waals materials according to the present invention have tunable band gaps ranging from about 0.1 eV to about 3.4 eV, or from about 0.1 eV to about 0.6 eV for stannanes, from about 1.3 eV to about 1.9 eV for germananes, from about 2.4 eV to about 3.4 eV for silicanes. In embodiments, the two-dimensional van der Waals materials have tunable band gaps of about 0.3 to about 1.6 to about 2.9 eV for Sn to Ge to Si. In embodiments, the band gap is more than about 0.1 eV or more than about 0.3 eV or more than about 0.6 eV or more than about 1.3 eV or or more than about 1.6 eV or more than about 2.4 eV or more than about 2.9 eV. In embodiments, the band gap is less than about 3.4 eV or less than about 2.9 eV or less than about 2.4 eV or less than about 1.6 eV or less than about 1.3 eV or less than about 0.6 eV or less than about 0.3 eV.

The van der Waals materials of the present invention may have a broad absorption over the visible wavelengths. For example, it may absorb from about 390 nm to about 700 nm.

In addition, the optical properties of the van der Waals materials of the present invention may be tuned based on the surface termination moiety. The covalent nature of the surface ligand allows for fine-tuning of both the two-dimensional layer band structure (band gap, mobility, effective masses, heights of the indirect and direct bands) as well as the potential interlayer thermal and electronic conductivities. Covalent surface termination of germanane with $CH_3$ not only increases the band gap by about 0.1 eV, but also enhances the thermal stability compared to GeH. The photoluminescence quantum yield is on the same order of magnitude as other single-layer metal chalcogenides, but does not have the stringent single-layer requirement to observe such band edge emission, making these materials intriguing building blocks for optoelectronic devices.

The optoelectric properties of the van der Waals materials of the present invention may be analyzed according to the standard techniques in the art. For example, diffuse reflective absorption (DRA) and photoluminescence (PL) measurements may be used to determine the optoelectric properties, such as the band gap and absorption wavelengths.

In embodiments, the van der Waals materials of the present invention may be thermally stable. For example, they may be stable up to about 300° C. or up to about 250° C. or up to about 200° C. In embodiments, the van der Waals materials of the present invention may be air stable. For example, they may be stable for at least 10 days, for at least 15 days, for at least 30 days, for at least 45 days, for at least 90 days, for at least 180 days, for at least 1 year, for at least 3 years or for at least 5 years. The thermal and air stability of the van der Waals materials may be analyzed according to the standard techniques in the art. For example, FTIR, thermogravimetric analysis (TGA), DRA, XRD, and Raman spectroscopy may be used.

Synthesis

In embodiments, the present invention provides a method of synthesizing two-dimensional van der Waals materials, such as germananes and stannanes. In embodiments, the van der Waals materials are synthesized via a one-step topotactic metathesis reaction of A-M$_2$ crystals with R—X, wherein A is an alkaline earth metal, such as calcium, barium or strontium, M is Ge or Sn, R is C$_{1-18}$ alkyl and X is halogen. In embodiments, the reaction occurs in the absence of solvent. In embodiments, a solvent may be used. The solvent may suitably aid in the solubilization of A-X$_2$, wherein A is an alkaline earth metal and X is halo. In embodiments, the solvent may be water. Suitably, the reaction occurs at a temperature at which R—X is a liquid.

In embodiments, a thin film of A-M$_2$ may be converted to M-R in the absence of a solvent. In embodiments, the thin film may be no more than about 200 nanometers in thickness.

In embodiments, organogermananes are synthesized via a one-step topotactic metathesis reaction of CaGe$_2$ crystals with R—X, wherein R is C$_{1-18}$ alkyl and X is halo. Bulk CaGe$_2$ crystals may be formed by annealing stoichiometric amounts of calcium and germanium. Alternatively, CaGe$_2$ crystals may be formed by co-deposition of Ca and Ge via vacuum evaporation, molecular beam epitaxy (MBE), or another suitable technique, or by growing CaGe$_2$ layers by vapor phase epitaxy (VPE) using Ca and Ge precursors via a technique such as metalorganic chemical vapor deposition (MOCVD). In another approach, a technique such as atomic layer epitaxy (ALE) or migration-enhanced epitaxy (MEE) can be employed in which the surface is exposed to the Ca and Ge beams or precursor gases separately and in alternation.

In embodiments, organostannanes are synthesized via a one-step topotactic metathesis reaction of BaSn$_2$ crystals with R—X, wherein R is C$_{1-18}$ alkyl and X is halo. Bulk BaSn$_2$ crystals may be formed by annealing stoichiometric amounts of barium and tin. Alternatively, BaSn$_2$ crystals may be formed by co-deposition of Ba and Sn via vacuum evaporation, molecular beam epitaxy (MBE), or another suitable technique, or by growing BaSn$_2$ layers by vapor phase epitaxy (VPE) using Ba and Sn precursors via a technique such as metalorganic chemical vapor deposition (MOCVD). In another approach, a technique such as atomic layer epitaxy (ALE) or migration-enhanced epitaxy (MEE) can be employed in which the surface is exposed to the Ba and Sn beams or precursor gases separately and in alternation.

Suitable R—X are shown in FIG. 2.

The Ge$_{1-x}$Sn$_x$R$^3$ materials may be synthesized in a similar manner as M-R from A-Ge$_{2-y}$Sn$_y$ crystals, wherein A is an alkaline earth metal and y is about 0 to about 2. In embodiments, the A-Ge$_{2-y}$Sn$_y$ crystals may be obtained by annealing the correct amounts of A, Ge and Sn.

In embodiments, y may be at least about 0.1, at least about 0.2, at least about 0.4, at least about 0.5, at least about 0.6, at least about 0.7, at least about 0.8, at least about 0.9, at least about 1.0, at least about 1.1, at least about 1.2, at least about 1.3, at least about 1.4, at least about 1.5, at least about 1.6, at least about 1.7, at least about 1.8, or at least about 1.9. In embodiments, y is less than about 2, less than about 1.9, less than about 1.8, less than about 1.7, less than about 1.6, less than about 1.5, less than about 1.4, less than about 1.3, less than about 1.2, less than about 1.1, less than about 1.0, less than about 0.9, less than about 0.8, less than about 0.7, less than about 0.6, less than about 0.5, less than about 0.4, less than about 0.3, less than about 0.2, or less than about 0.1.

In embodiments, A is Ba when y is about 1.5 to about 2; A is Sr when y is about 0.8 to about 1.5; and A is Ca when y is about 0 to about 0.8.

Alternatively, the Ge$_{1-x}$Sn$_x$R$^3$ materials may be synthesized using the epitaxial growth of precursor phases CaGe$_2$ and BaSn$_2$ on Ge(111). For example, the epitaxial CaGe$_2$ layer then converted into GeR$^1$ and the epitaxial BaSn$_2$ layer into SnR$^2$. Then, bilayer heterostructures can be prepared by transferring the GeR$^1$ layer onto SnR$^2$, using a soft lithographic transfer approach.

As another example, the creation of multilayer heterostructures of GeR$_x$Sn$_x$Ge$_{1-x}$R$^3$ could be achieved through epitaxial growth of graded CaGe$_{2-y}$Sn$_y$ on Ge(111) followed by topotactic metathesis reaction of the CaGe$_2$/CaGe$_{2-y}$Sn$_y$ with the organohalide.

The Ge$_{1-x}$Si$_x$R$^6$ materials may be synthesized in a similar manner as M-from CaGe$_{2-y}$Si$_y$ crystals, wherein y is about 0 to about 2. In embodiments, the CaGe$_{2-y}$Si$_y$ crystals may be obtained by annealing the correct amounts of Ca, Ge and Si.

In embodiments, y may be at least about 0.1, at least about 0.2, at least about 0.4, at least about 0.5, at least about 0.6, at least about 0.7, at least about 0.8, at least about 0.9, at least about 1.0, at least about 1.1, at least about 1.2, at least about 1.3, at least about 1.4, at least about 1.5, at least about 1.6, at least about 1.7, at least about 1.8, or at least about 1.9. In embodiments, y is less than about 2, less than about 1.9, less than about 1.8, less than about 1.7, less than about 1.6, less than about 1.5, less than about 1.4, less than about 1.3, less than about 1.2, less than about 1.1, less than about 1.0, less than about 0.9, less than about 0.8, less than about 0.7, less than about 0.6, less than about 0.5, less than about 0.4, less than about 0.3, less than about 0.2, or less than about 0.1.

Alternatively, the Ge$_{1-x}$Si$_x$R$^6$ materials may be synthesized using the epitaxial growth of precursor phases CaGe$_2$ and CaSi$_2$ on Ge(111). For example, the epitaxial CaGe$_2$ layer then converted into GeR$^4$ and the epitaxial CaSi$_2$ layer into SiR$^5$. Then, bilayer heterostructures can be prepared by transferring the GeR$^4$ layer onto SiR$^5$, using a soft lithographic transfer approach.

As another example, the creation of multilayer heterostructures of GeR$_x$Si$_x$Ge$_{1-x}$R$^6$ could be achieved through epitaxial growth of graded CaGe$_{2-y}$Si$_y$ on Ge(111) followed by topotactic metathesis reaction of the CaGe$_2$/CaGe$_{2-y}$Si$_y$ with the organohalide.

Uses

As mentioned above, the two-dimensional van der Waals materials of the present invention are suitably direct band gap semiconductors and may have enhanced thermal stability. Thus, in embodiments, the compounds of the present invention may be used in optoelectronic devices, such as transistors, light-emitting devices, such as light-emitting diodes and lasers, and light-absorbing devices, such as photovoltaics and photodetectors.

EXAMPLES

Figure 4:
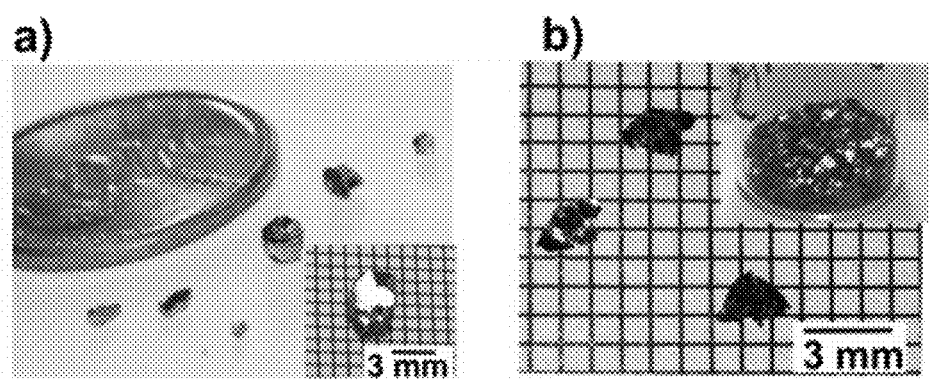
FIG. 4 shows optical images of a) $CaGe_2$ and b) GeH crystals with select crystals on graph paper with a 1 mm grid (inset).
Figure 5:
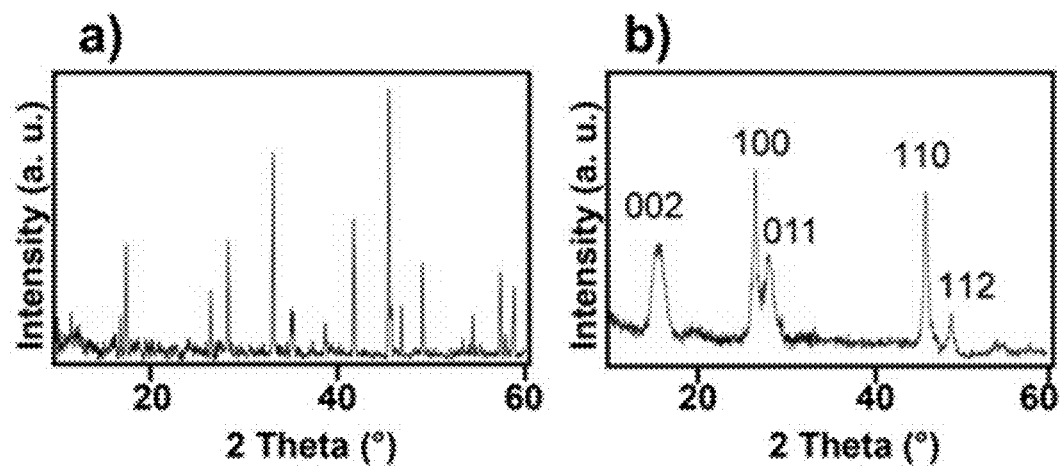
FIG. 5 shows powder XRD pattern of a) $CaGe_2$ and b) GeH.

Example 1. Synthesis and Characterization of the Hydrogen-Terminated Germanane Described below is the synthesis and characterization of hydrogen-terminated germanane. The hydrogen-terminated germanane were synthesized by topotactic deintercalation of β-CaGe$_2$ in aqueous HCl at −40° C. for at least eight days (FIG. 3). 2-6 mm crystals of β-CaGe$_2$ were first synthesized by sealing stoichiometric ratios of Ca and Ge in a quartz tube, annealing to 950-1050° C., and cooling down over a period of 2-10 days (FIG. 4a). High purity CaGe$_2$ was confirmed via powder X-ray diffraction (FIG. 5). After HCl treatment, the product was filtered and washed with methanol to remove residual CaCl$_2$, yielding crystallites of GeH that are 2-3 mm in diameter and <100 μm in thickness (FIG. 4b). X-ray diffraction analysis of GeH confirmed that it can be fit to a 2H unit cell (2 GeH layers per hexagonal c-unit cell spacing) with a=3.880 Å and c=11.04 Å (5.5 Å per layer). Compared to the original CaGe$_2$ unit cell parameters of a=3.987 Å, c=30.0582 Å, (6 layer stacking, c/6=5.097 Å), the hydrogen-terminated germanane is slightly contracted in the a direction but expanded in the c-direction due to the replacement of Ca$^{2+}$ with 2 Ge—H bonds between each layer. These lattice parameters do not correspond to any of the previously reported allotropes of germanium. The narrower full-width-half-maximum (FWHM) of the (100) and (110) diffraction reflections (~0.4° 2θ) compared to the (002), (011) and (112) peaks (~1.3° 2θ) indicates that there is a significant amount of disorder along the c axis, which is common in layered materials. This disorder along the c axis precludes further structure determination via Rietveld analysis.

Figure 6:
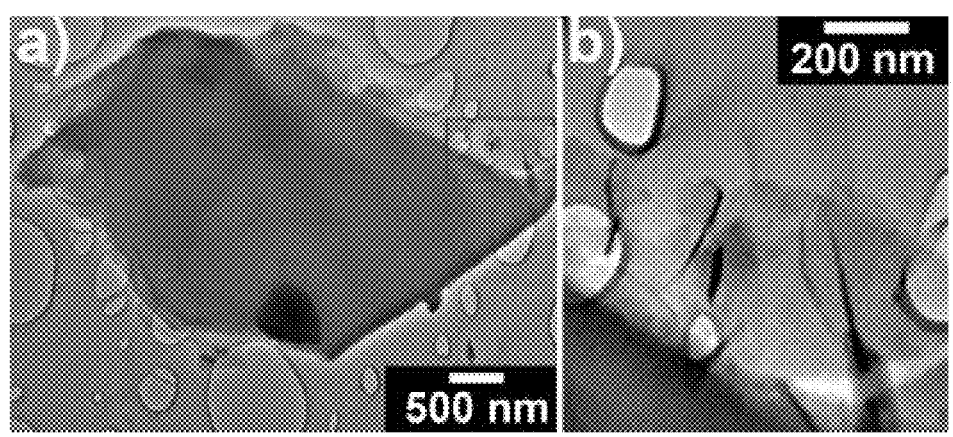
FIG. 6 shows a) low magnification and b) magnified TEM micrograph of GeH platelets.
Figure 7:
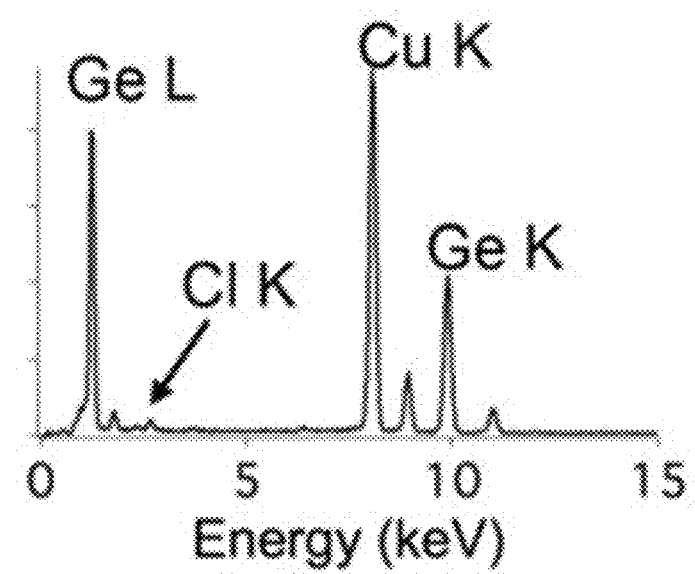
FIG. 7 is an energy dispersive X-ray Spectroscopy of the GeH sheets.
Figure 8:
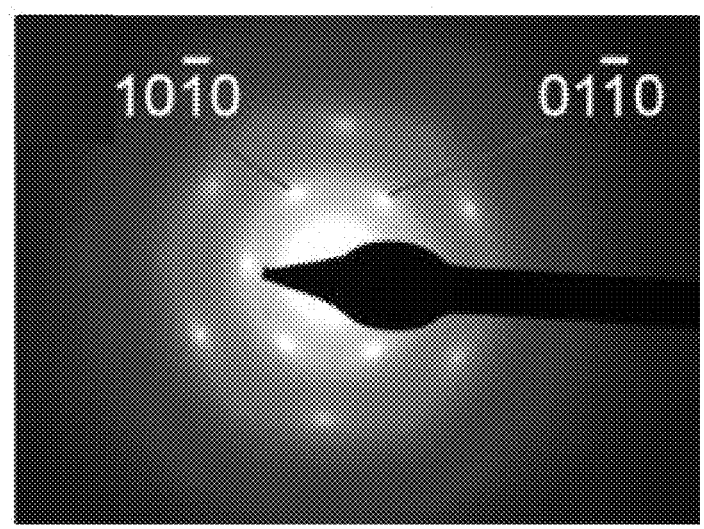
FIG. 8 shows an electron diffraction pattern of platelets collected down the 0001 zone axis.

Transmission electron microscopy analysis indicates the hydrogen-terminated germanane has a layered morphology with individual layers having less contrast than the 10 nm lacey carbon support grid (FIG. 6). The energy dispersive X-ray spectrum has a strong Ge signal, an absence of Ca and O signals and the presence of trace amounts of Cl. The Cl:Ge ratio was estimated to be 2:98 (FIG. 7). FIG. 8 depicts an electron diffraction pattern taken orthogonal to the layers, showing a hexagonal arrangement of diffraction peaks that occur in the a and b directions. This data further confirms that the crystallinity of the germanium layered framework is preserved upon HCl treatment, and there is a strong registration in the stacking between each layer. The GeH electron diffraction pattern can be indexed to a simple hexagonal unit cell with a=b≈4.0 Å, assuming a [001] zone axis.

Figure 9:
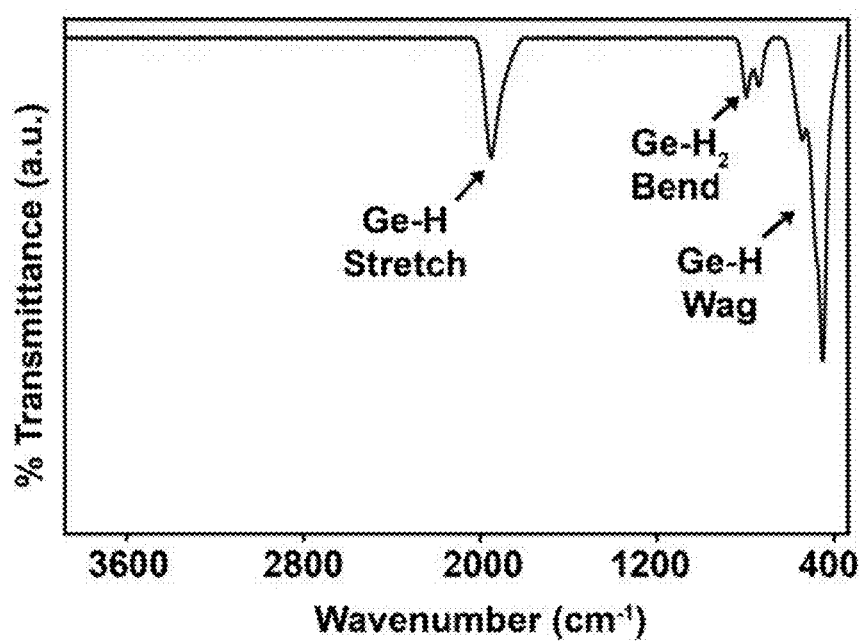
FIG. 9 shows a transmission-mode FTIR of GeH.
Figure 10:
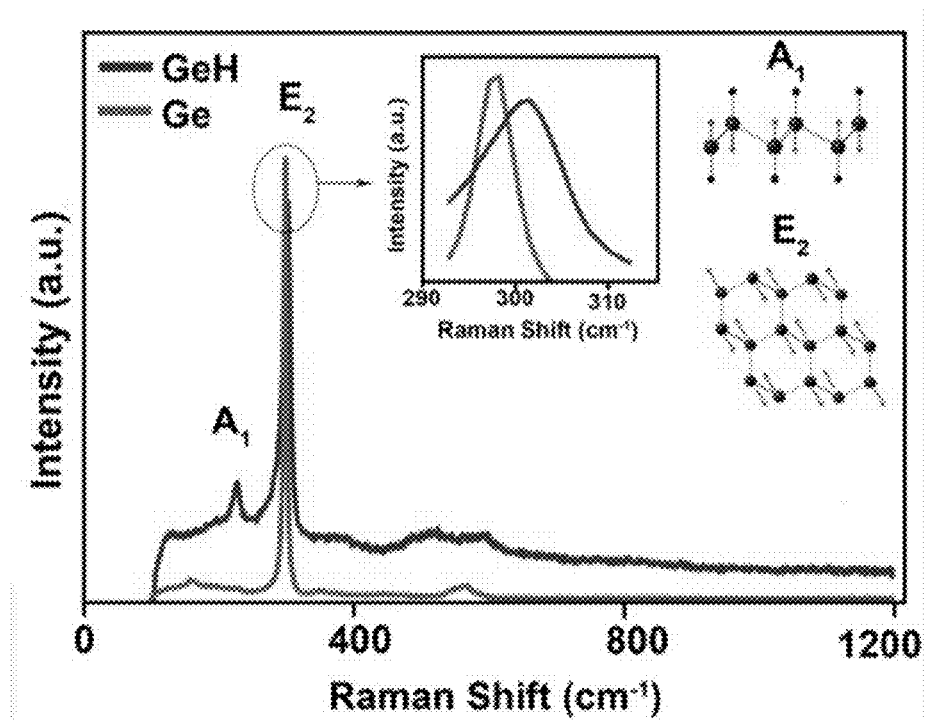
FIG. 10 shows a raman spectrum of GeH and Ge powder, highlighting the difference in energy of the E2 peak between GeH and Ge (middle inset).
Figure 11:
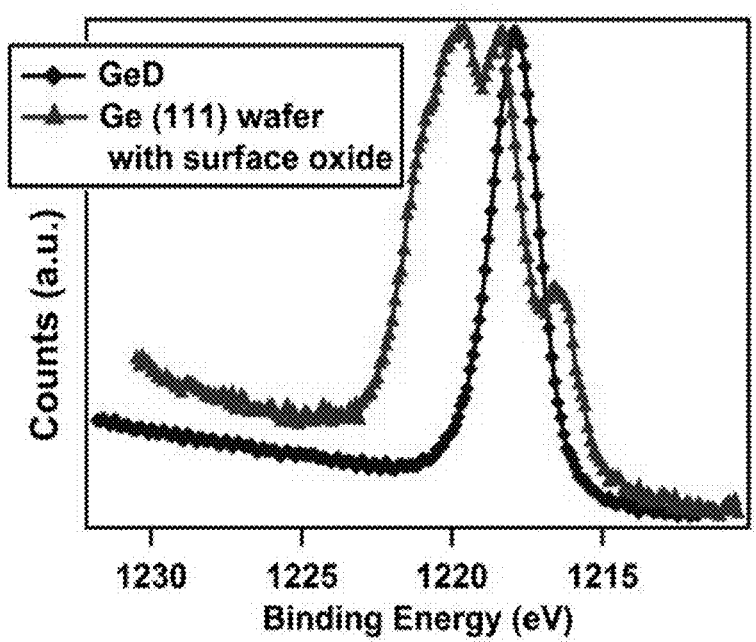
FIG. 11 is an XPS spectrum of the Ge 2p peak for GeH and a Ge(111) wafer with native surface oxide.
Figure 12:
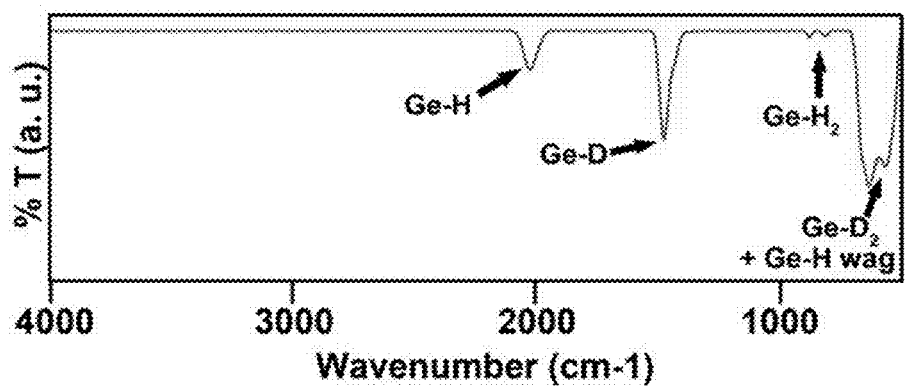
FIG. 12 is a Mid-FTIR spectrum of GeD.

To further confirm hydrogen termination, FTIR, Raman spectroscopy, and X-ray photoelectron spectroscopy (XPS) were performed on the hydrogen-terminated germanane (FIG. 9-11). Transmission mode FTIR of samples, which were ground up and pressed into KBr pellets, show extremely strong Ge—H stretching and multiple wagging modes at ~2000 cm$^{-1}$ and 570, 507, and 475 cm$^{-1}$, respectively. Additionally, weak vibrational modes at 770 cm$^{-1}$ and 825 cm$^{-1}$ are observed. These two vibrations also occur in the spectra of amorphous Ge0.7:H0.3 thin films. It is known that the weak Ge—H2 at 770 cm$^{-1}$ can vary from 750-770 cm$^{-1}$. The absence of any stretching modes at ~2060 cm$^{-1}$, precludes the presence of Ge—H3. Thus, the data suggests that these vibrations correspond to Ge—H2 bond bending modes from neighboring Ge atoms at the edges of each crystalline germanane sheet, and/or to Ge—H2 bonds within the lattice arising from Ge vacancies. The presence of the broad, intense Ge—O—Ge and Ge—O vibrational modes that occur between 800 cm$^{-1}$ and 1000 cm$^{-1}$ is not observed. To confirm that these vibrational modes originate from Ge—H2 and not Ge—O—Ge, GeD were prepared by treating CaGe$_2$ in 95% deuterated DCl/D$_2$O, and the FTIR spectrum was collected (FIG. 12). The 825 cm$^{-1}$ and 770 cm$^{-1}$ vibrational modes significantly decrease to negligible absorbance, and new Ge-D2 modes at 586 cm$^{-1}$ and 514 cm$^{-1}$ appear with residual Ge—H wagging modes. This is generally consistent with the change in reduced mass upon deuteration, and these vibrational frequencies are also apparent in amorphous Ge0.7:D0.3 films.

FIG. 10 shows the main Ge—Ge stretch in GeH occurs at 302 cm$^{-1}$, which is slightly blue-shifted compared to the 297 cm$^{-1}$ E2 Raman mode for crystalline germanium. In addition, a second vibrational mode emerges at 228 cm$^{-1}$. ab initio calculations were performed for the Γ-point phonon modes in GeH using Perdew-Burke-Ernzerhof (PBE) functionals as implemented in VASP. These calculations predict the presence of Ge-based A1 and E2 Raman modes (assuming a C6v point group) that occur at 223 cm$^{-1}$ and 289 cm$^{-1}$, respectively, which are in relatively close agreement with the observed Raman modes, considering that the theoretical bond lengths and lattice constant (a=should correspond to lower frequencies than found in experiment due to the well-known d-3/2 scaling of frequencies with bond lengths). Following similar logic, the Ge—Ge bondlength in germanane should be very close to that in bulk Ge, within ~0.1 Å. The symmetries of the vibrational modes are shown in the FIG. 10 inset.

XPS measurements also demonstrate a single germanium oxidation state. XPS of the Ge 2p3/2 peak for GeH shows a single peak at 1217.8 eV, which is indicative of Ge$^{+1}$. A shift in the Ge 2p3/2 peak energy from Ge0 (1217.0 eV) is anticipated because hydrogen is more electronegative than germanium (FIG. 11). A control Ge(11) wafer with surface oxide shows a mixture of germanium oxidation states ranging from Ge$^0$ (1217.0 eV) to Ge$^{2+}$ (1218.9 eV) to Ge$^{4+}$ (1221.4 eV).

Figure 13:
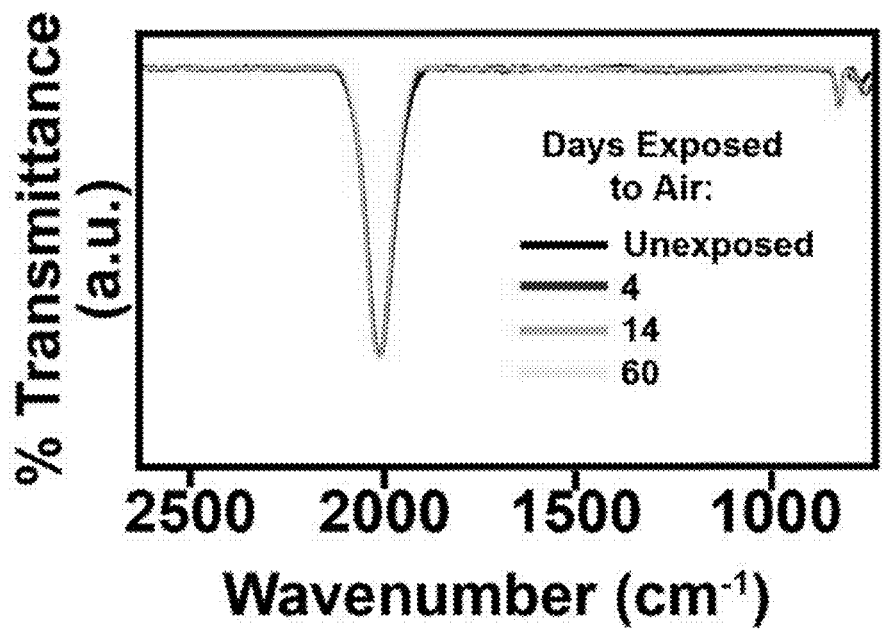
FIG. 13 shows time dependent reflection mode FTIR of a GeH platelet after exposure to ambient atmosphere for up to 60 days, collected via reflection mode, highlighting minimal changes in the relative intensity of the Ge—H to Ge—O vibrations.
Figure 14:
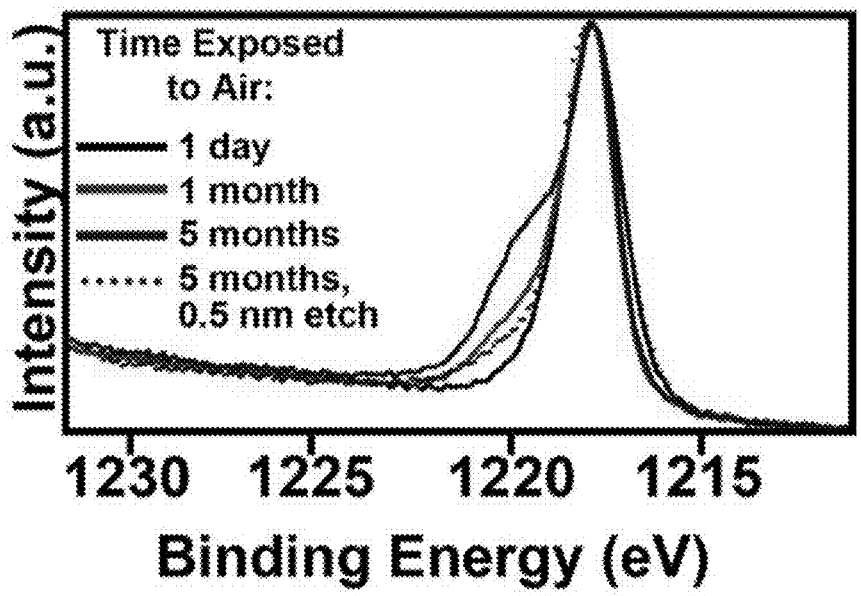
FIG. 14 shows time dependent XPS spectra of germanane immediately after exposure to atmosphere, after 1 day, and 5 months, followed by Ar etching by 0.5 nm.

The potential utility of germanane for any optoelectronic or sensing device strongly hinges on its air and temperature stability. A time-dependent FTIR study was conducted to determine if Ge—O vibrational modes in the 800-1000 cm$^{-1}$ range emerge after exposure to an ambient atmosphere. After 60 days, virtually no change was observed in this range, suggesting that the bulk of GeH resists oxidation (FIG. 13). Additionally, time dependent XPS was performed to probe changes in the Ge oxidation state of the surface after exposing these layered GeH crystals to air (FIG. 14), and the percentage of each germanium oxidation state for all spectra was calculated by applying a standard Gaussian fit. After 1 month of exposure to air, a Ge$^{2+/3+}$ shoulder emerges at ~1219.3 eV (19.5% Ge$^{2+/3+}$). This peak becomes more intense after 5 months of air exposure (29.7% Ge$^{2+/3+}$). After Ar etching the top 0.5 nm (<1 layer), the Ge$^{2+/3+}$ almost completely disappears, with approximately 10.1% Ge$^{2+/3+}$ remaining. Together, the XPS and FTIR suggest that only the surface becomes oxidized over time.

Figure 15:
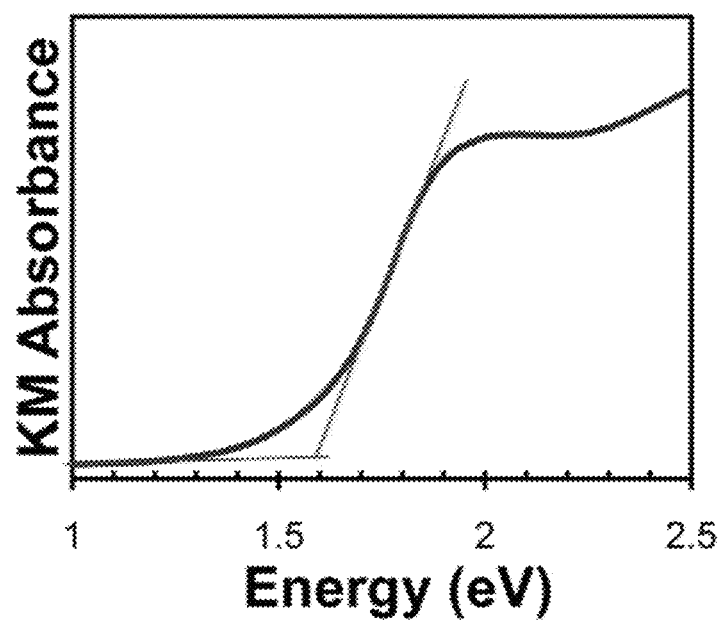
FIG. 15 is a DRA spectrum of GeH plotted as (hvα) vs. photon energy highlighting a 1.59 eV band gap.
Figure 16:
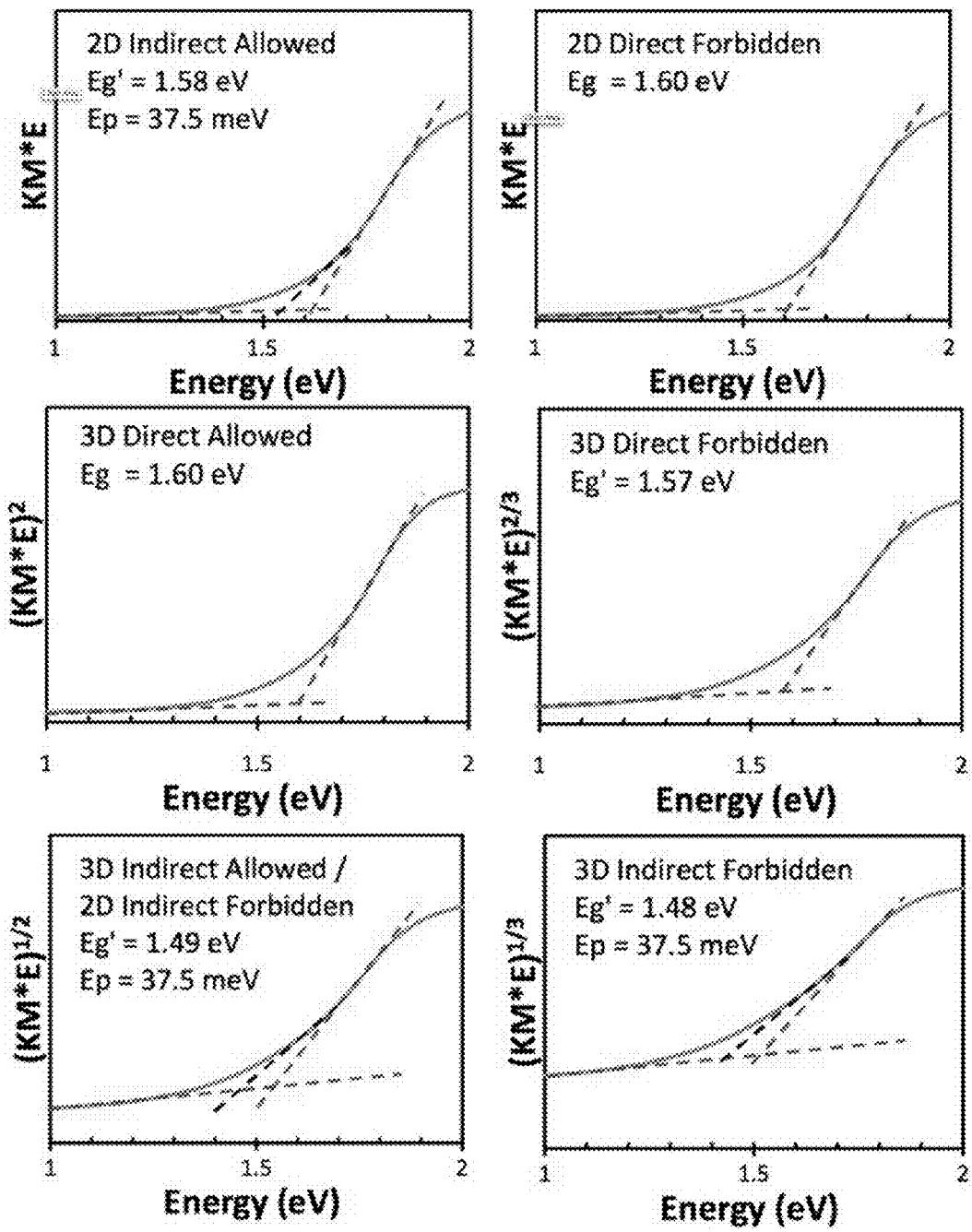
FIG. 16 shows fits of the absorption spectrum of unannealled GeH to different band structures, according to Tauc/Davis-Mott expressions of 2D densities of states and 3D densities of states. A 37.5 phonon vibration (deduced via the 300 $cm^{-1}$ Raman shift) was determined.

The optical properties of germanane were investigated by diffuse reflectance absorption (DRA) spectroscopy. The silver-black material has a broad absorption over visible wavelengths, and a linear approximation of the absorption edge suggests a band gap of approximately 1.59 eV (FIG. 15). The Tauc/Davis-Mott expression for materials with 2D densities of states, predicts that the absorbance A(ℏω) at photon energy hυ near the band edge would be a step function with a discontinuity in absorbance at the band gap, if the band gap was direct allowed. If the band gap was indirect allowed, the absorbance would be proportional to (ℏ ω−Eg'±Ep) where Eg' is the indirect gap, and Ep is the energy of a particular phonon mode. However, it has been experimentally established that the Tauc/Davis-Mott approximations of absorption cannot unambiguously determine the transition mechanism for fundamental absorption for bulk materials with 2D densities of states. The absorbance was modeled assuming direct-allowed, direct-forbidden, indirect-allowed and indirect-forbidden gaps using both 2D and 3D densities of states (FIG. 16). All of these plots estimated fundamental gaps ranging from 1.48 to 1.60 eV. These analyses are complicated by a broad Urbach edge at the lower end of the absorption tail, which is often indicative of a large doping concentration or disorder. The presence of photoluminescence is often a stronger test of a direct band gap. There was negligible observance of any photoluminescence from 1.1-1.8 eV when exciting from 1.38-1.96 eV at temperatures ranging from 14-300 K.

Figure 17:
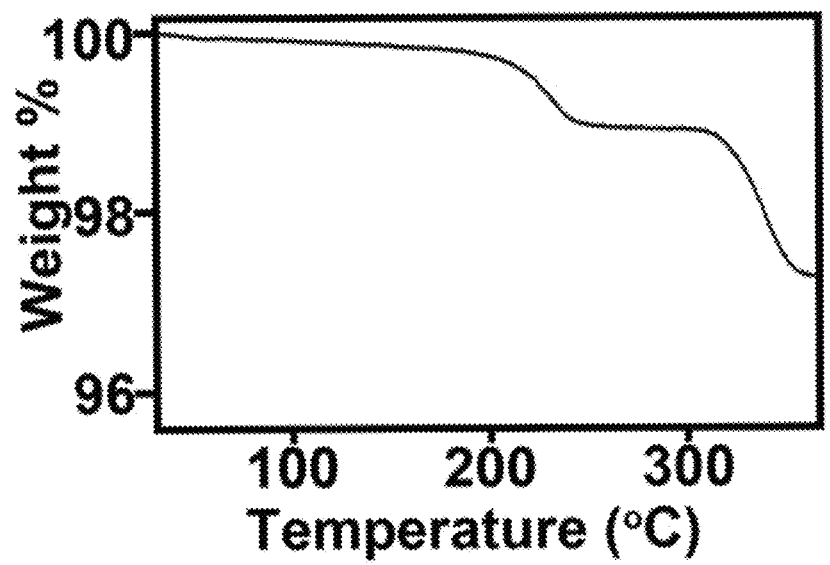
FIG. 17 is a TGA analysis of GeH.
Figure 18:
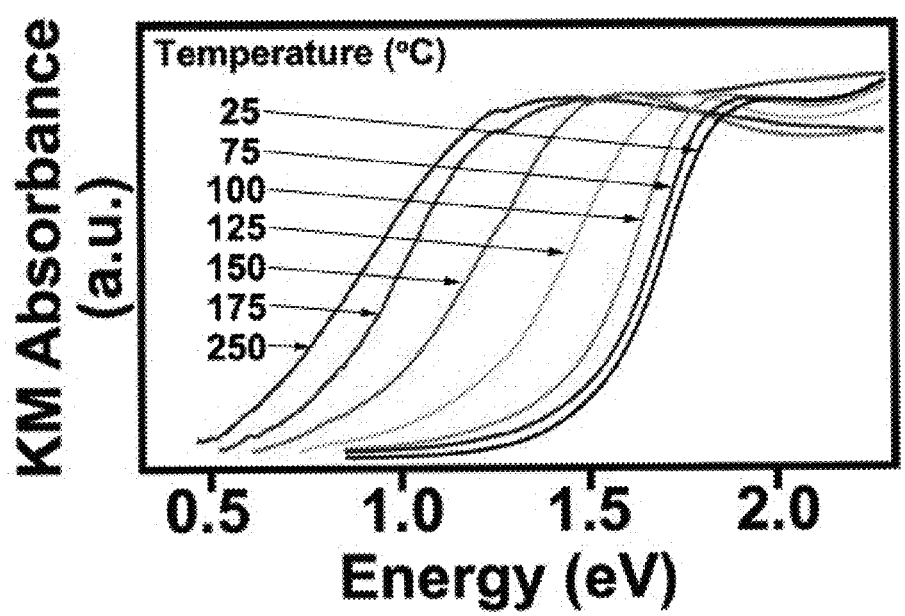
FIG. 18 are DRA spectra of GeH.
Figure 19:
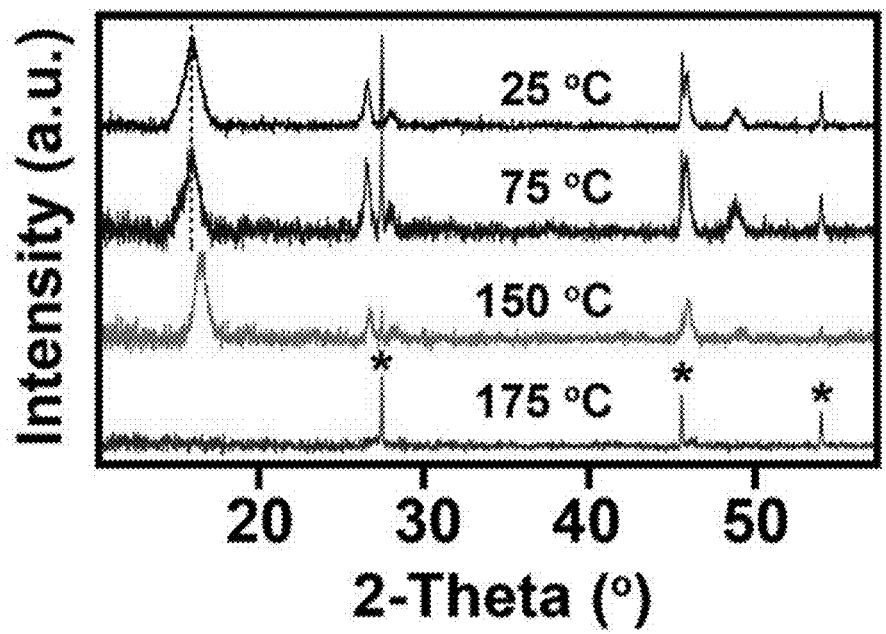
FIG. 19 are XRD patterns of GeH.
Figure 20:
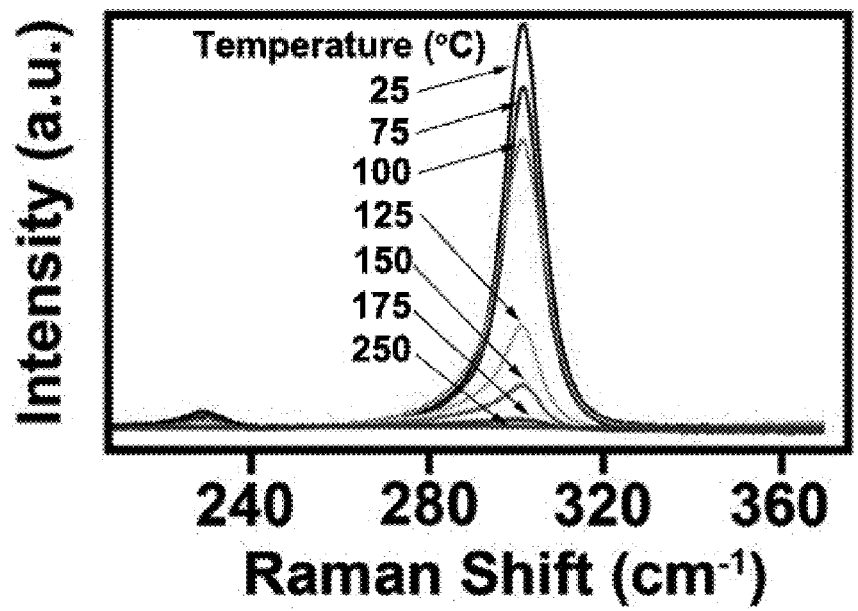
FIG. 20 are Raman spectra of GeH measured after four hour annealing treatments at various temperatures in 5% $H_2$/Ar.

The temperature stability of germanane was also investigated via thermogravimetric analysis (TGA), DRA, XRD, and Raman upon annealing at a range of temperatures in 5% $H_2$/Ar. TGA shows a ~1.1% mass loss at 200-250° C., which is close to the expected mass loss of 1 equivalent of Hydrogen in GeH, as well as a 1.7% mass loss of that occurs between 320 to 355° C. (FIG. 17). The second mass loss likely corresponds to the loss of Cl (3.6% molar). X-ray fluorescence analysis further supports this, as there is approximately a one order of magnitude decrease in the chlorine intensity after annealing at 375° C. Furthermore, it has been reported in previous temperature programmed desorption studies that Cl desorbs off of germanium at temperatures ranging from 300-350° C. However, there is a significant change in the absorption spectrum when annealing at temperatures above 75° C. The absorption onset, as detected by DRA, red shifts by 0.06 eV upon annealing at 75° C. (FIG. 18). The absorption profile continues to red-shift with higher temperature annealing until 250° C. when the absorption onset (0.58 eV) goes below that of bulk germanium (0.67). Previous studies have reported that amorphous Ge thin films have band gaps lower than that of bulk germanium (0.50 vs. 0.67 eV), and amorphous hydrogenated germanium films have larger band gaps (1.1 eV). No obvious change appears in the XRD patterns (FIG. 19) until 150° C., at which point the c axis decreases from c=11.04 Å to c=10.70 Å and the FWHM of this 002 reflection decreases from 1.3o 2θ to 0.8o 2θ. The diffraction pattern demonstrates complete amorphization upon annealing at 175° C. Raman spectroscopy shows a consistent decrease in the intensity of both the Ge—Ge and Ge—H modes as a function of annealing temperature (FIG. 20). After 175° C., there is ~2 order magnitude decrease in the Raman scattering intensity of both the E2 and A1 modes. Taken together, this suggests that amorphization occurs at temperatures well below that of dehydrogenation (200-250° C.). It is hypothesized, without being bound to any particular theory, that the low-temperature amorphization, the broadness of the 001 reflections, and the lack of observed PL, are consequences of the presence of trace percentages of Ge—Cl bonds. This would potentially explain the observed decrease in the c-parameter and FWHM of the 001 reflections at 150° C. The observed diffraction pattern at this temperature is indicative of local domains of pure GeH that did not undergo amorphization due to the lack of nearby chlorine.

Figure 22:
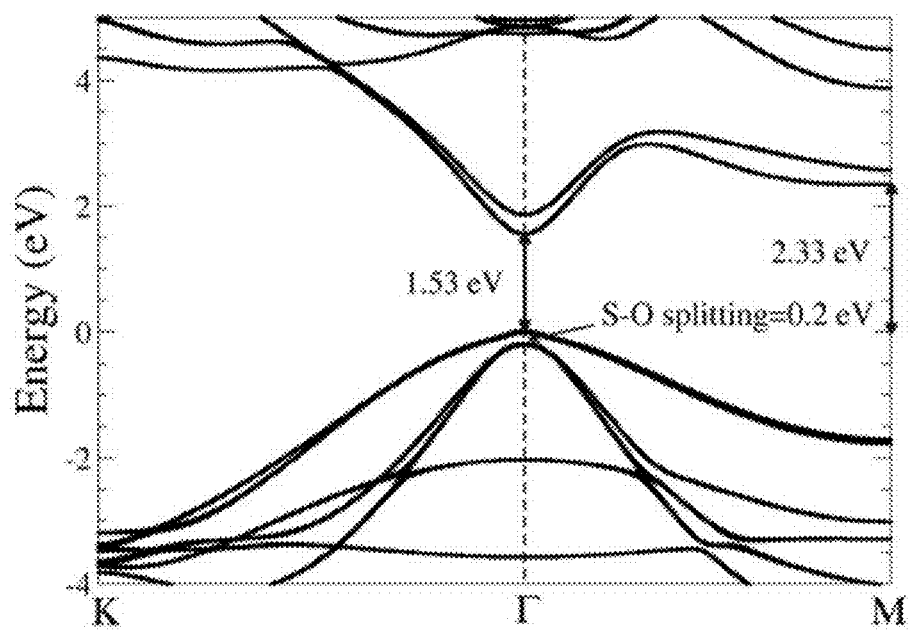
FIG. 22 shows electronic band structure of bulk 2 layer GeH calculated using HSE-06 theory including spin-orbit coupling from K-Γ-M.
Figure 23:
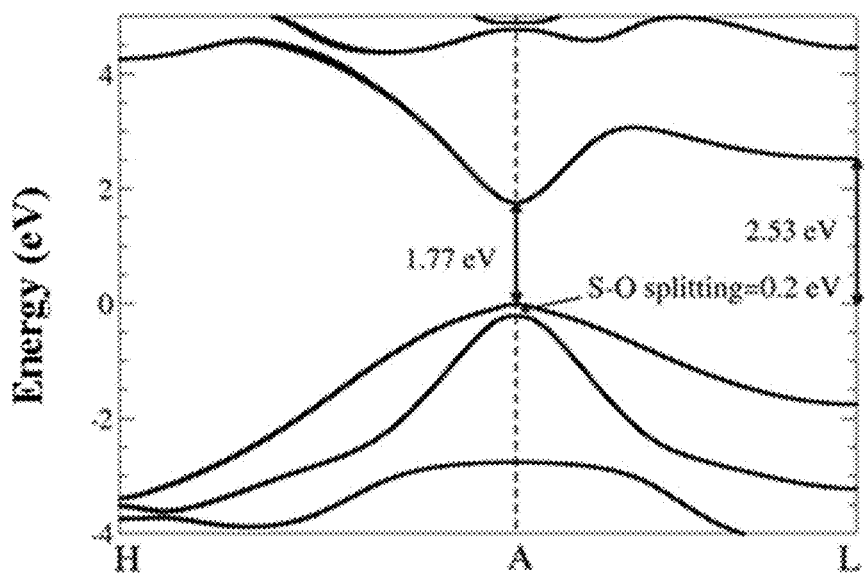
FIG. 23 shows electronic band structure of bulk 2 layer GeH calculated using HSE-06 theory including spin-orbit coupling from H-A-L.
Figure 24:
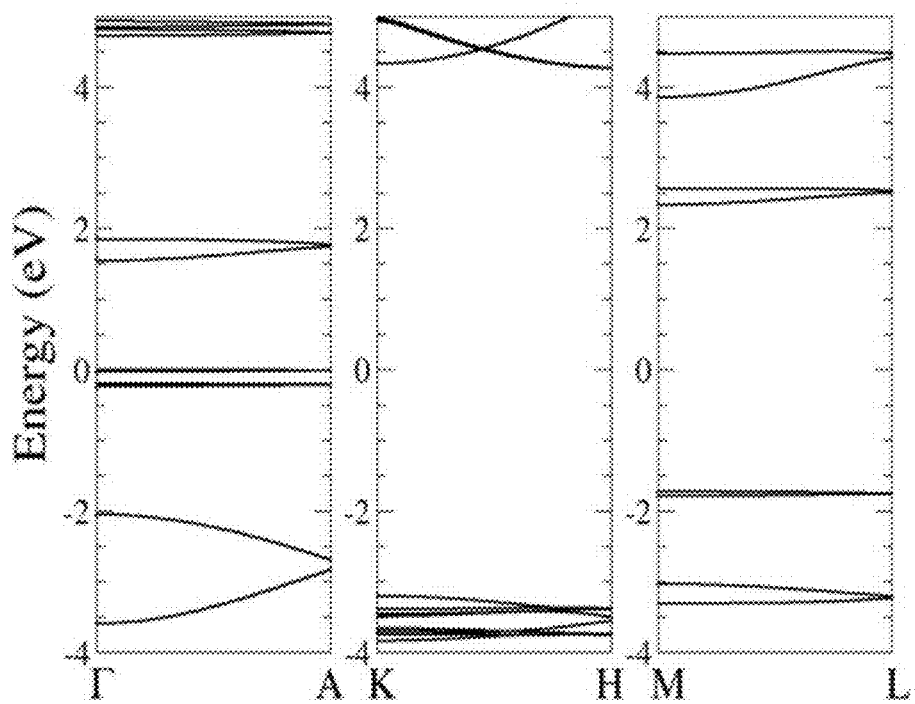
FIG. 24 shows electronic band structure of bulk 2 layer GeH calculated using HSE-06 theory including spin-orbit coupling from Γ-A, K—H and M-L.

Band structure calculations suggest that germanane is a direct band gap material both as isolated layers and in the crystal structure having two layers per unit cell. The density functional theory (DFT) code VASP was used to optimize the geometry, and calculate the band structure of isolated single layer and 2-layer unit cell GeH. The interactions between cores and electrons were described for relaxation by projector augmented wave (PAW) pseudopotentials within the Perdew-Burke-Ernzerhof (PBE) exchange-correlation function with a plane-wave cutoff energy of 600 eV. Van der Waals interactions between the layers were included using the DFT-D2 method by Grimme. For the two-layer structure, the unit cell was modeled as a P63mc unit cell with relaxed lattice parameters of a=4.05 Å, and c=10.56 Å, thus having a 5.3 Å layer spacing. However, these values may contain error since the c lattice constant, determined mostly by the weak interlayer van der Waals interactions, were found to depend very sensitively on the exact computational parameters, resulting in an uncertainty of ~1 Å. In return, the a lattice constant changes with variations in c. For example, if c is fixed to the experimental value of 11.04 Å, a relaxes to 4.01 Å, which is identical to the isolated-layer value. For the isolated single layer structure, calculations were performed in a unit cell with 20 Å of additional vacuum between GeH layers. To obtain an accurate description of the band gap in this system, the hybrid HSE06 exchange-correlation function was utilized. With this function, we obtain a direct gap at the Γ point of 1.56 eV for an isolated layer (FIG. 21), and 1.53 eV for the 2-layer unit cell (FIG. 22-24), which is in agreement with the observed experimental band gap. The calculated band gap for the two layer unit cell at the A point of the Brillouin zone is ~1.77 eV. The difference in energy between the conduction band minimum at the M point and the valence band maximum at Γ is 2.48 eV and 2.33 eV for an isolated layer, and 2-layer unit cell, respectively. In both cases, spin-orbit splitting at the Γ valence band maximum is 0.2 eV.

Figure 21:
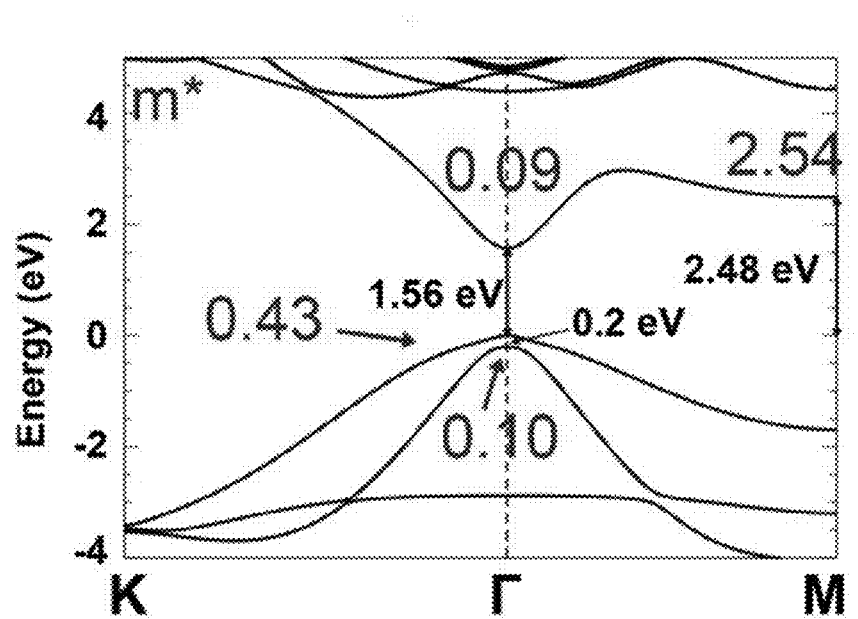
FIG. 21 shows electronic band structure of an isolated single layer of GeH calculated using HSE-06 theory including spin-orbit coupling predicting a 1.56 eV direct band gap.

Additionally, the effective masses of the conduction and valence bands at each extremum were calculated for the isolated single layer and are shown in FIG. 21. In bulk crystalline germanium, the conduction band minima occur in the 4 equivalent valleys at the L <111> point which have much higher effective mass ($meL^*$=1.64) than the conduction band valleys at Γ ($meΓ^*$=0.041). However, since GeH can be thought of as hydrogen-terminated isolated (111) sheets of germanium, the L wavevector in the Brillouin zone are effectively eliminated. The phonon-limited electronic mobility for an isolated single layer was calculated having a high mobility of 18195 $cm^2$/Vs. This 5× increase in electron mobility from the bulk Ge (3900 $cm^2$/Vs) is consistent with the reduced electron effective mass in GeH.

Also, using the EXCITING-CODE, the Bethe-Salpeter equation was solved to account for the excitonic effects. The scissors operator was used to obtain a band gap of 1.53 eV for the two layer unit cell (to correspond with the HSE calculated band gap value). Within this theoretical framework, an excitonic binding energy was calculated to be 0.28 eV for the two layer unit cell. No excitonic phenomena were observed in the absorption or photoluminescence in the samples. However, this 0.28 eV exciton binding energy may explain the previously observed 0.45 eV red shift between the absorption onset and photoluminescence of epitaxial GeH thin films.

Example 2. Exfoliation of Hydrogen-Terminated Germanane into Single Sheets

Figure 25:
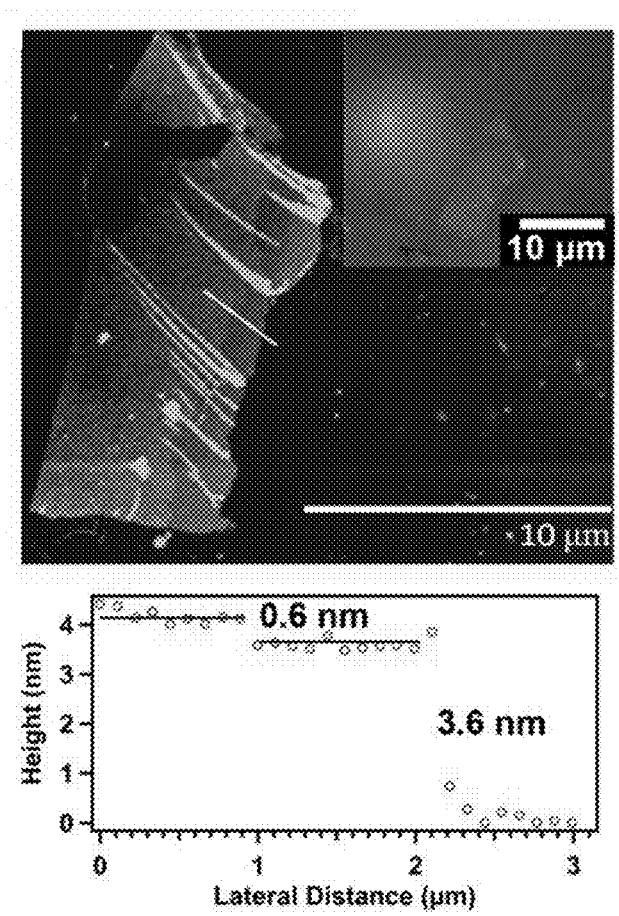
FIG. 25 is an AFM micrograph (top), height profile (bottom), and optical micrograph (inset) of few layer GeH deposited on 110 nm $SiO_2$/Si.
Figure 26:
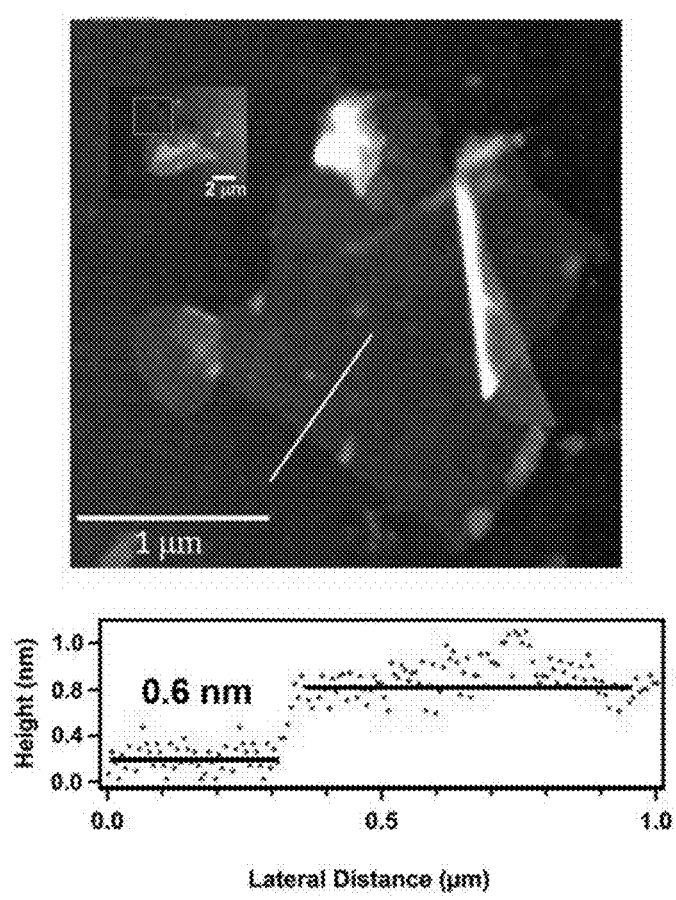
FIG. 26 is an AFM micrograph (top), and height profile (bottom) of single layer thick GeH sheet.

Hydrogen-terminated germanane can be mechanically exfoliated into single sheets. Similar to most layered crystal structures, the GeH crystal structure is held together predominantly via van der Waals bonding. By incorporating van der Waals corrections into the PBE simulation, the interlayer binding energy for GeH was found to be nearly entirely dominated by van der Waals interaction with a value of 72 meV per Ge atom, which is in the same range as the calculated 53.5 meV per C atom in graphite. Therefore both scotch tape and polydimethylsiloxane were used to exfoliate few and single layer thick sheets onto Si substrates with a wide range of $SiO_2$ thicknesses (100-165, 275-345 nm) to attain maximum contrast by optical microscopy. Few-layer and single-layer sheets were visible by optical microscopy, with 110 nm and 300 nm thick $SiO_2$ substrates providing optimal contrast. FIG. 25 shows an AFM image, optical micrograph, and corresponding height profile for a 6-7 layer thick germanane flake. FIG. 26 shows an AFM image, optical micrograph and the corresponding height profile for a 2 μm×2 μm single GeH layer exfoliated onto a 100 nm thick $SiO_2$/Si substrate. The observed height (~6 Å) agrees well with the expected value of 5.5 Å for a single layer, since it is well known that differences in the attractive potentials between the AFM tip, the substrate, and the layered material can often cause the measured AFM thickness to be larger than the expected value. The weak Raman intensities of few layer GeH, the photothermal degradation at laser intensities above 40 kW/cm$^2$ and the overlap of the two E2 and A1 Raman modes with higher order silicon substrate Raman modes prevents the collection of thickness-dependent Raman maps on conventional $SiO_2$/Si substrates.

Example 3. Synthesis and Characterization of the Methyl-Terminated Germanane

Figure 27:
FIG. 27 shows a biphasic CH$_3$I/H$_2$O reaction setup.

To synthesize $CaGe_2$ crystals, Ca and Ge were loaded into a quartz tube with stoichiometric ratio. The quartz tube was sealed under vacuum and annealed at 950-1050° C. for 16-20 hours and then slowly cooled down to room temperature. To synthesize $GeCH_3$, the $CaGe_2$ crystals were loaded into an extraction thimble, fully immersed in iodomethane (Sigma Aldrich), with a separated distilled water phase outside in the beaker and stir bar at the bottom of the extraction thimble (FIG. 27). The reaction was performed at room temperature for a week. Then the exfoliated flakes were rinsed with isopropanol (Sigma Aldrich), concentrated HCl(aq) (Fisher, Certified ACS Plus) followed by isopropanol. The sample was then dried on a Schlenk line at room temperature. For all thermal stability study experiments, the room temperature sample was annealed at different temperatures in flowing 5% $H_2$ in Ar, then cooled down and characterized at room temperature.

Powder XRD (Bruker D8 powder X-ray diffractometer, Rigaku MiniFlexII X-Ray diffractometer), and Single crystal XRD (Nonius Kappa CCD diffractometer) were used to study the structure of $GeCH_3$. FTIR measurements were collected on a Perkin-Elmer Frontier Dual-Range FIR/MidIR spectrometer that was loaded in an Ar-filled glovebox. XPS was collected using a Kratos Axis Ultra X-ray photoelectron spectrometer equipped with a monochromated (Al) X-ray gun. The AFM images were collected on a Bruker AXS Dimension Icon Atomic/Magnetic Force Microscope with Scan Asyst. DRA measurements (PerkinElmer Lambda950 UV/Vis Spectrometer) and PL (Cary Eclipse Fluorescence Spectrophotometer) measurements were conducted to study the optical properties of the bulk solid crystals. In the PL measurements, the excitation wavelength was set to 380 nm, the excitation and emission slit widths were set to 20 nm and 5 nm, respectively. The absolute Quantum Yield of the solid samples was measured with the Quanta-phi (HORIBA Scientific) assembled in Fluorolog (HORIBA Scientific). The temperature dependent and the thickness dependent PL measurements were collected using a Renishaw InVia Raman equipped with a CCD detector upon excitation using a 633 nm HeNe laser at a power density of ~24 mW/cm$^2$, with a laser spot size of ~2 μm diameter. To collect the thickness dependent measurement, $GeCH_3$ was exfoliated onto 285 nm $SiO_2$/Si. The thicknesses of these flakes were measured by AFM to identify exfoliated flakes that had regions of relatively uniform thickness larger than the excitation spot size. The weighted average height from the AFM measurement was used to determine the thickness. For the temperature dependent PL, exfoliated flakes were annealed at different temperatures in 5% $H_2$/Ar, and their PL was recollected on the same flake after cooling down to room temperature. The same trend was observed for three different exfoliated flakes. Thermogravimetric Analysis (Q-500 thermogravimetric analyzer) was collected in flowing $N_2$ at 10° C. min$^{-1}$. Elemental Analysis (Atlantic Microlab Inc) of the C/H ratio was collected to determine the ratio of $CH_3$-termination to H-termination.

Figure 28:
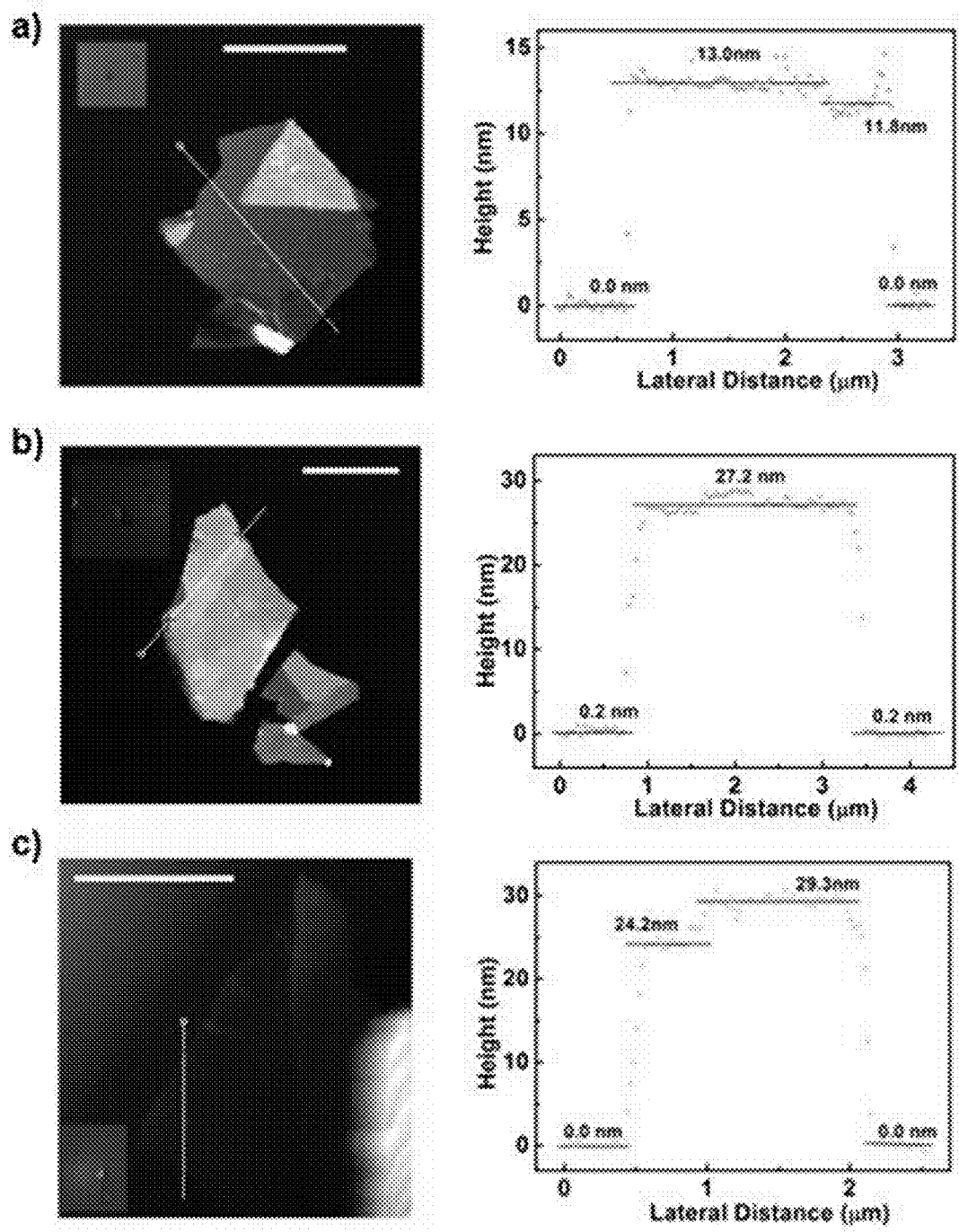
FIGS. 28 & 29 show AFM images and height profiles of exfoliated GeCH$_3$ flakes with different thickness. The scale bar in d is in 1 μm, and all other scale bars are in 2 μm.
Figure 29:
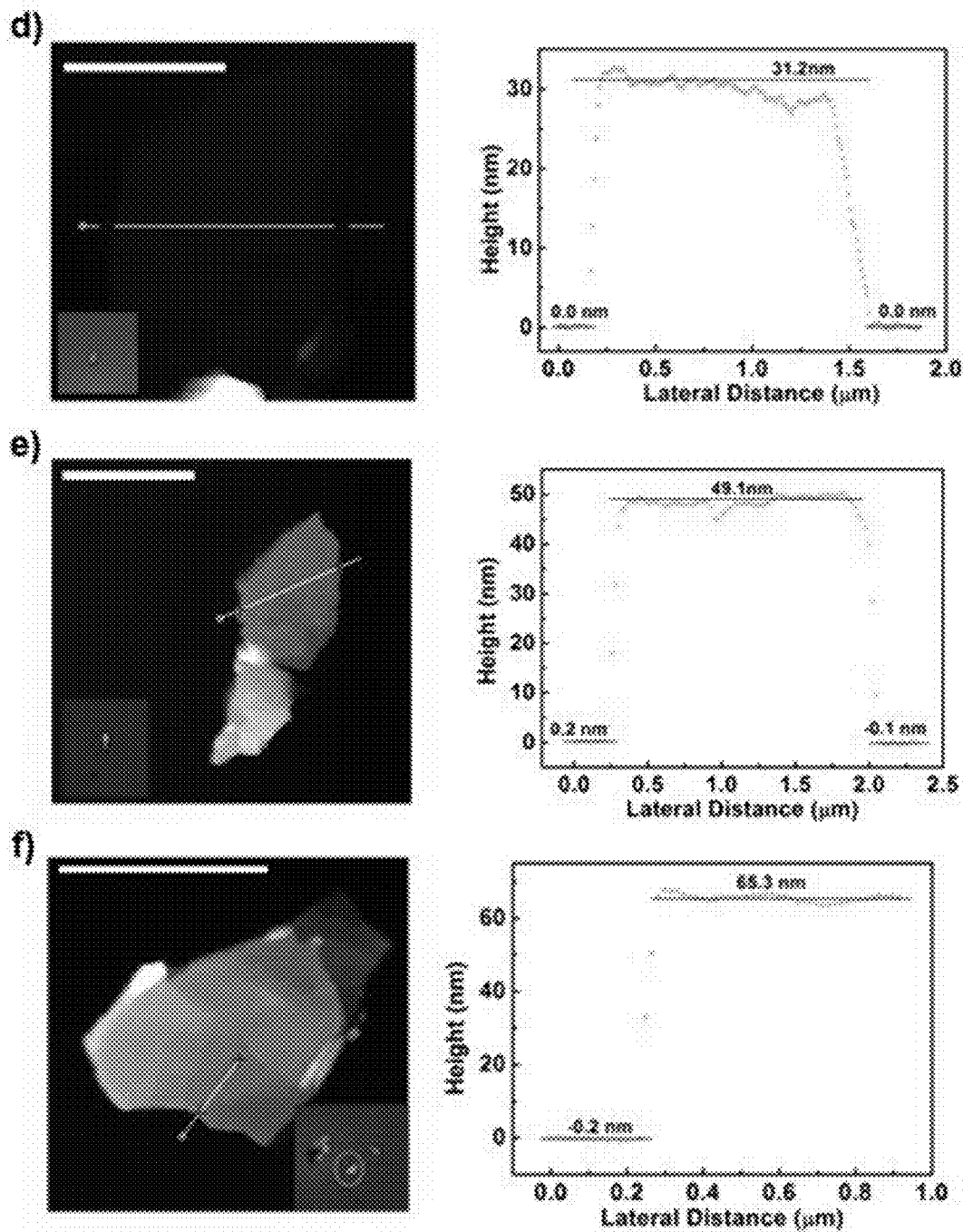

To study the PL intensity of $GeCH_3$ flakes with different thickness, the bulk $GeCH_3$ flakes were exfoliated onto 285 nm $SiO_2$/Si substrate with kapton tape. The tape residue was cleaned with acetone and then by isopropanol, followed by a $N_2$ blow dry to clean the residue solvent on the substrate. The thickness of these flakes was confirmed by AFM before the PL measurement. The AFM images are shown in FIG. 28-29, the color of the dots in AFM height profiles corresponds to the color of the PL spectra in FIG. 30.

Density functional theory (DFT) calculations were performed using the Vienna Ab initio simulation package (VASP). The effect of the core electrons was included using projector augmented wave (PAW) pseudopotentials. To simulate $GeCH_3$ monolayers, a supercell was used with a vacuum of 20 Å and with the in-plane lattice parameter fixed to the experimental value a=3.97 Å. Bilayer $GeCH_3$ was simulated using a supercell with lattice parameters fixed to a=3.97 Å and c=17.26 Å. Relaxation of the ionic positions was done using the Perdew-Burke-Ernzerhof exchange correlation functional with a plane-wave cutoff energy of 600 eV and a 9×9×1 Monkhorst Pack k-point mesh. To obtain an accurate description of the band gap, high-level calculations were performed based on the HSE06 hybrid functional.

Figure 31:
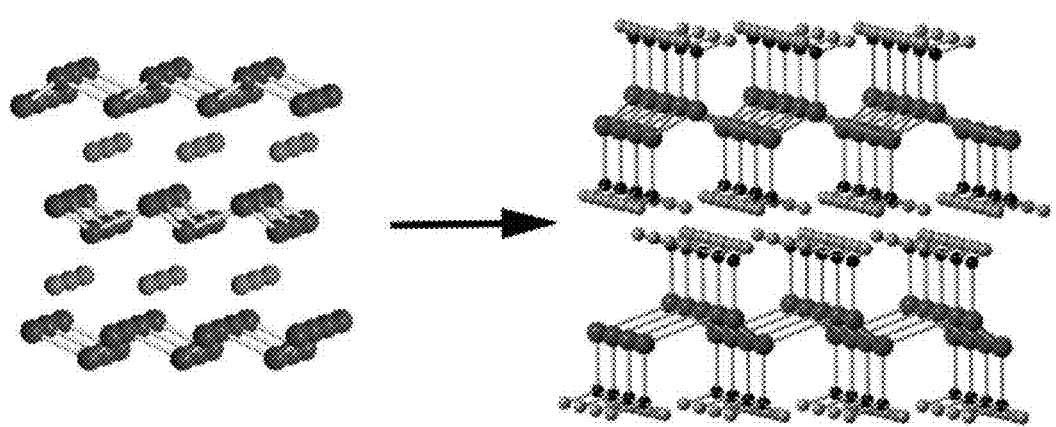
FIG. 31 is a schematic illustration of conversion of CaGe$_2$ (left) into GeCH$_3$ (right).
Figure 32:
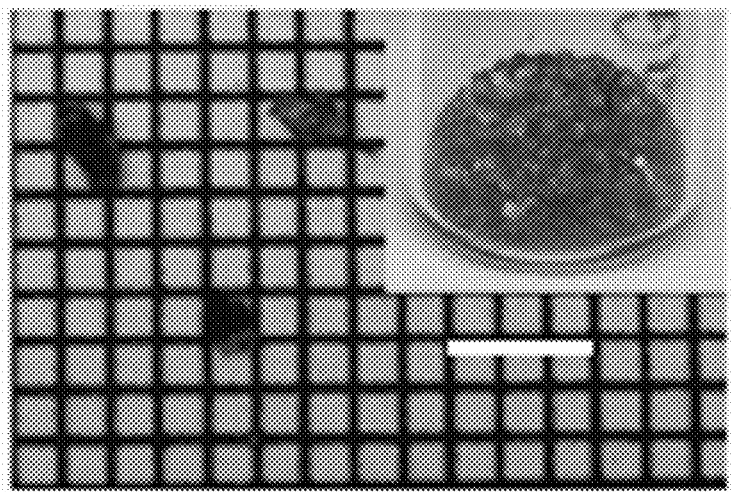
FIG. 32 shows optical images of GeCH$_3$ crystals with select crystals on graph paper with a 1 mm grid. Scale bar, 3 mm.
Figure 33:
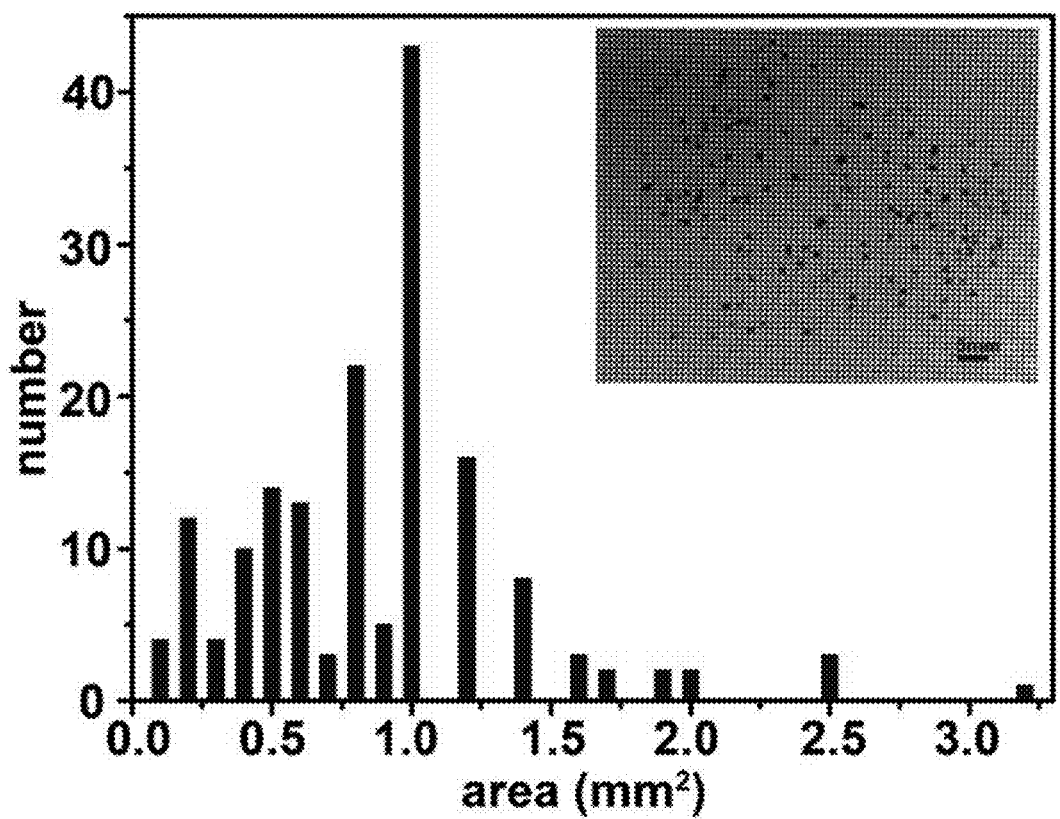
FIG. 33 is a size distribution of synthesized GeCH$_3$ flakes.
Figure 34:
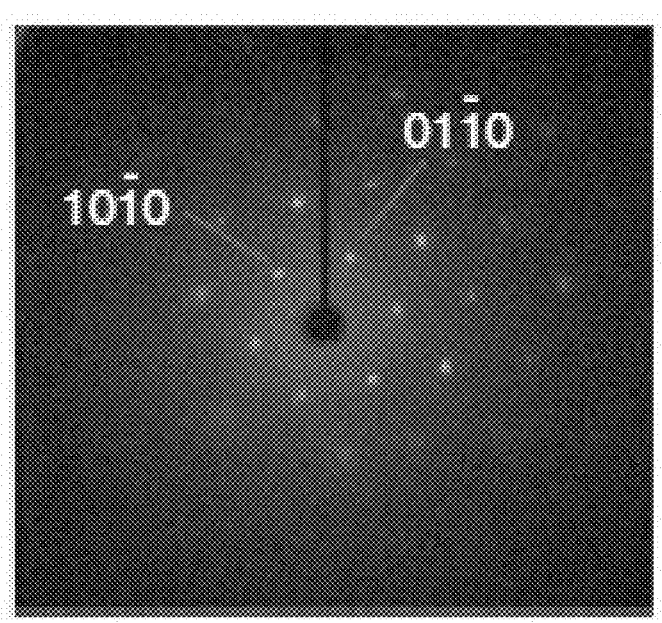
FIG. 34 is a single-crystal XRD pattern of GeCH$_3$ collected down the [001] zone axis.
Figure 35:
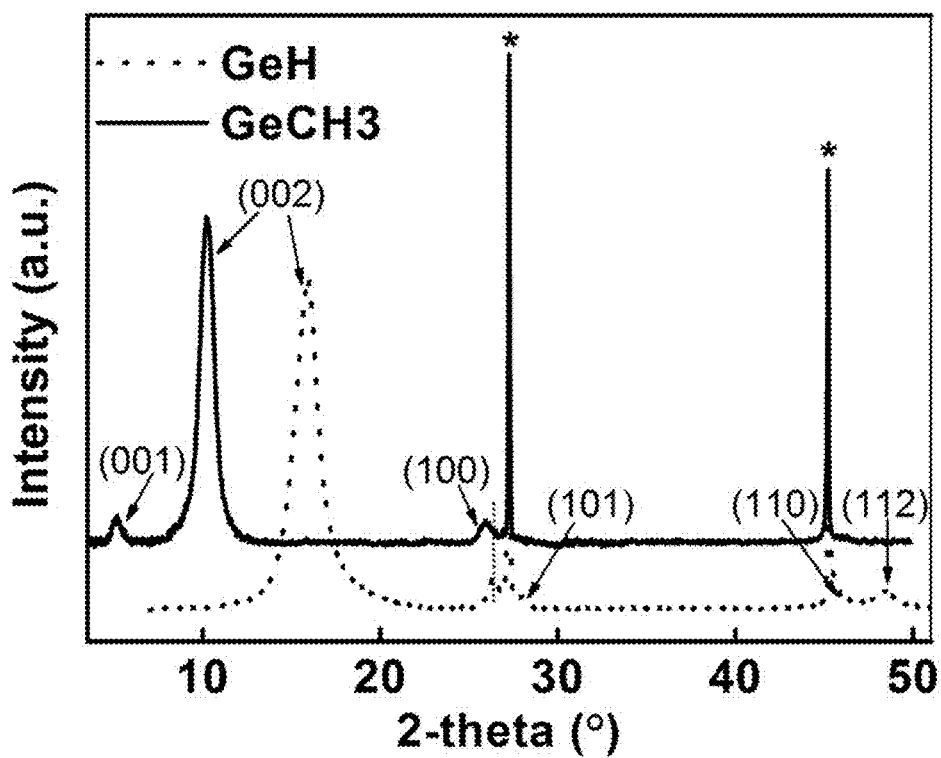
FIG. 35 shows powder XRD patterns of GeH (dotted) and GeCH$_3$ (solid). The starred peaks correspond to diffraction reflections of an internal Ge standard. The dotted line highlights the changes in the 100 reflections between GeH and GeCH$_3$.
Figure 36:
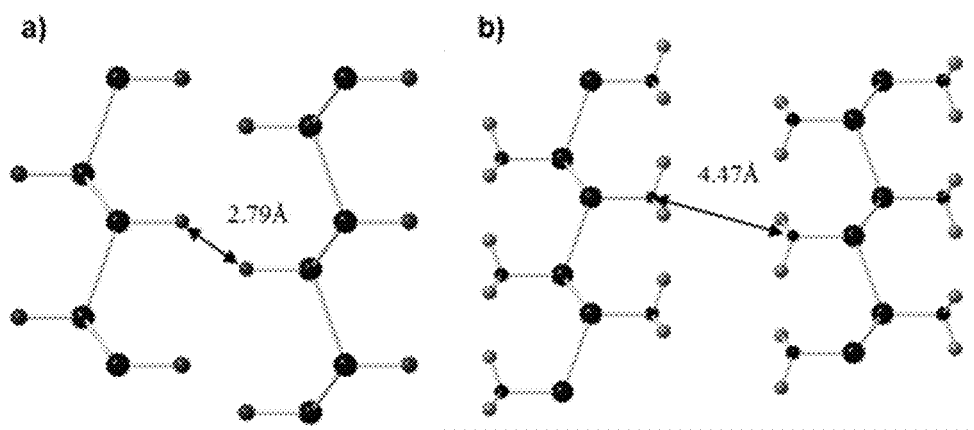
FIG. 36 shows structural models of GeH (a) and GeCH$_3$ (b) structures.

The crystal structure of $CaGe_2$ consists of hexagonal, puckered sp$^3$ layers of Ge-atoms that are separated by $Ca^{2+}$ ions (FIG. 31). It was hypothesized, without being bound to any particular theory, that the anionic Ge— on the surface and edges of the crystals could react topotactically in an $SN_2$ or methathesis-like fashion with a small organic molecule such as $CH_3I$, to form a Ge—$CH_3$ bond along with $CaI_2$. The expansion of the lattice would allow the precursors to diffuse inward and the reaction would proceed to completion. However, in initial experiments with pure $CH_3I$, only the surface layers of $CaGe_2$ had reacted, likely due to the low solubility of $CaI_2$. Instead, a biphasic $CH_3I/H_2O$ solvent reaction was developed, in which 2-3 mm crystals of $CaGe_2$ are fully immersed in $CH_3I$, while $CaI_2$ is transferred into the $H_2O$ layer (FIG. 27). After rinsing in concentrated HCl to remove any trace residual $CaI_2$, and then isopropanol, the reaction yields crystals of $GeCH_3$ that are ~1 mm in diameter and <100 μm in thickness (FIG. 32 and FIG. 33). Single-Crystal X-ray diffraction (XRD) analysis (FIG. 34) shows that each one of the crystallites is a single crystal having a hexagonal spacing of a=3.96 Å, however the interlayer turbostratic disorder and curvature of these crystallites preclude determination of the c-axis spacing. Powder XRD analysis (FIG. 35) of GeCH$_3$ confirms that it can be fit to a 2H unit cell (2 GeCH$_3$ layers per hexagonal unit cell spacing) with a=3.97 Å and c=17.26 Å (8.63 Å per layer). This corresponds to a 0.09 Å expansion in the a-direction and a 3.1 Å increase per layer compared to GeH, which has lattice parameters of a=3.880 Å and c=11.04 Å (5.50 Å per layer). The 3.1 Å increase is approximately twice the difference between the Ge—C bond length (1.95 Å) and the Ge—H bond length (1.52 Å), plus twice the difference between the van der Waals radii of —CH$_3$ (2.0 Å) and —H (1.2 Å), further indicating substitution of the —H substituent with a —CH$_3$ substituent (FIG. 36).

Figure 37:
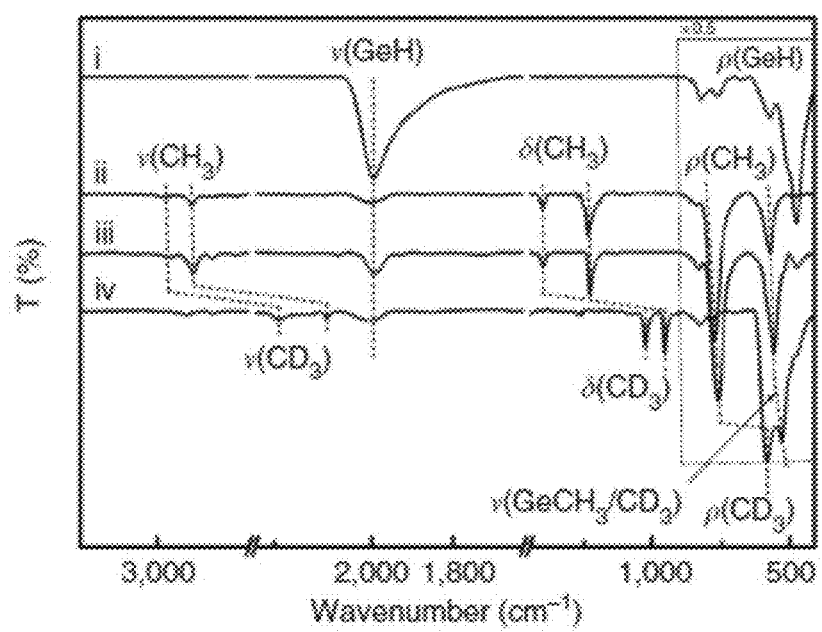
FIG. 37 shows FTIR spectra of GeH (i), GeCH$_3$ (ii), Ge$^{13}$CH$_3$ (iii) and GeCD$_3$ (iv).
Figure 38:
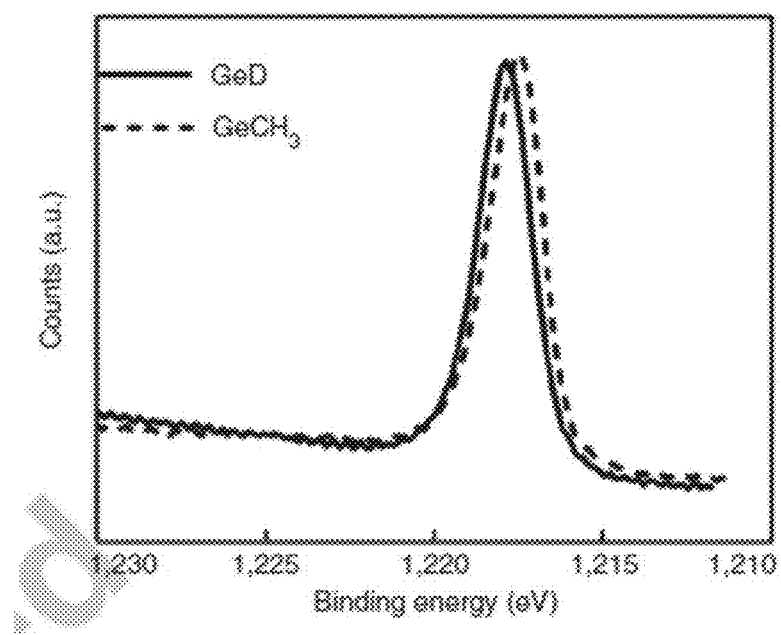
FIG. 38 is an XPS spectra of the Ge 2p3/2 peak for GeH (solid line) and GeCH$_3$ (dashed line).

Transmission-mode Fourier Transform Infrared spectroscopy further confirms the —CH$_3$ surface termination in GeCH$_3$ (FIG. 37) and that the sample is free of residual oxide. In GeCH$_3$, the major Ge—H stretching frequency at ~2,000 cm$^{-1}$ is nearly completely gone and replaced by a Ge—C stretch that occurs at 573 cm$^{-1}$. The other major modes that are observed in GeCH$_3$ correspond to —CH$_3$ stretching at 2907 and 2974 cm$^{-1}$, —CH$_3$ bending at 1403 and 1237 cm$^{-1}$, and —CH$_3$ rocking at 778 cm$^{-1}$. The residual amount of Ge—H stretching suggests that there exists a small percentage of —H termination, and elemental analysis suggests that 90%±10% of the Germanium atoms are terminated with —CH$_3$. The residual —H could result either from the minor solubility of H$_2$O in CH$_3$I, or during the washing process. To further confirm the identity of each vibrational mode, Ge$^{13}$CH$_3$ and GeCD$_3$ were created. In Ge$^{13}$CH$_3$, the Ge—C stretch shifts down to 558 cm$^{-1}$, and the other —CH$_3$ vibrational modes slightly decrease by 1-10 cm$^{-1}$ (Table 1). There is a significant change in the vibrational energies of GeCD$_3$, as the —CD$_3$ stretching modes are shifted to 2240 and 2116 cm$^{-1}$, the —CD$_3$ bending mode decreases to 1024 and 954 cm$^{-1}$, the —CD$_3$ rocking mode decreases to 584 cm$^{-1}$, and the Ge—CD$_3$ stretch decreases to 530 cm$^{-1}$ (Table 1). As the 778 cm$^{-1}$ CH$_3$ rocking mode can possibly mask the existence of any residual Ge—O—Ge or Ge—O vibrational modes, which normally occur from 800-1000 cm$^{-1}$, the shift of this rocking mode in GeCD$_3$ allows elucidation of any residual Ge—O—Ge or Ge—O. The only vibrational modes observed in this region for GeCD$_3$ are the 770 and 830 cm$^{-1}$ vibrations that correspond to bond-bending Ge—H2 modes from nearest neighbor Ge atoms at the crystal edges. X-ray Photoelectron Spectroscopy (XPS) measurements indicate a single Germanium +1 oxidation state (FIG. 38), further suggesting that GeO$_2$ and other surface oxides are not present. The Ge 2p3/2 peak occurs at 1217.5 eV, which is slightly shifted compared to the observed 1217.8 eV peak of GeH, but consistent with CH$_3$-terminated Ge(111). The slight shift to lower XPS binding energy is consistent with previously observed XPS spectra of —H or —CH$_3$ terminated silicon surfaces.

TABLE 1

Comparison of vibration modes of GeCH$_3$, GeCD$_3$ and Ge$^{13}$CH$_3$.

| Vibration modes* | GeCH$_3$ | Ge$^{13}$CH$_3$ | GeCD$_3$ |
|---|---|---|---|
| —CH$_3$ stretch | 2907, 2974 | 2902, 2972 | 2240, 2116 |
| —CH$_3$ bend | 1403, 1237 | 1402, 1230 | 1024, 954 |
| —CH$_3$ rock | 778 | 764 | 584 |
| Ge—CH$_3$ stretch | 573 | 558 | 530 |

*Here, C refers to either C or $^{13}$C, H refers to either H or D depending on the isotope listed. The units for all vibrations are in cm$^{-1}$.

Figure 30:
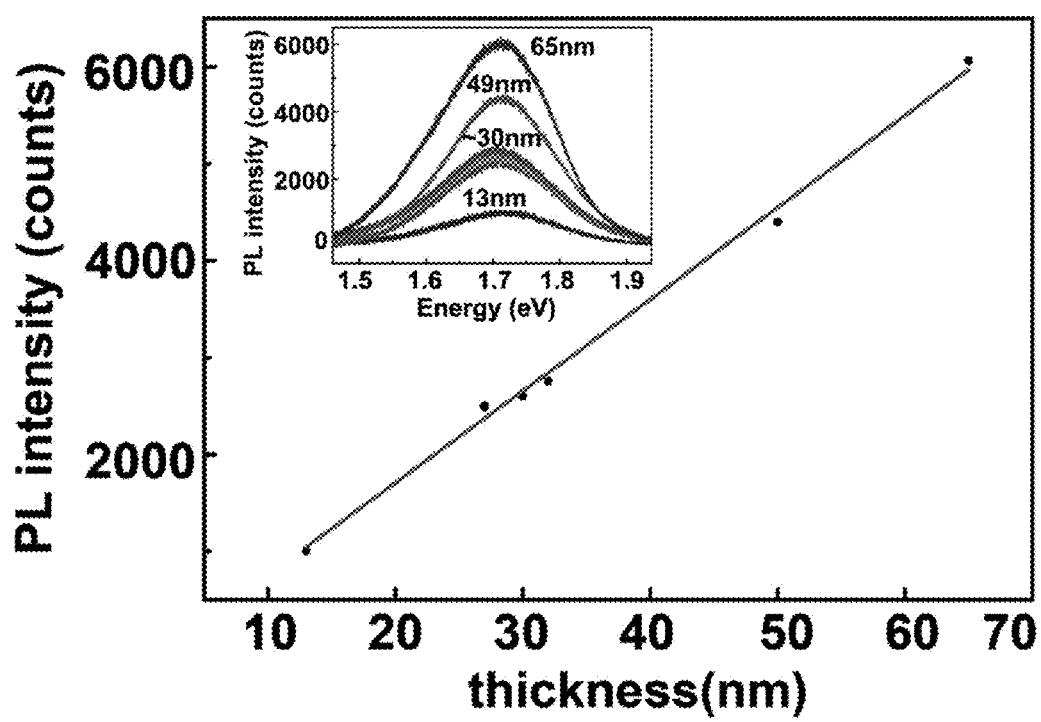
FIG. 30 shows PL intensity of exfoliated GeCH$_3$ thin flakes having average thicknesses ranging from 13-65 nm. Inset is the raw photoluminescence spectra of flakes with varying thicknesses.
Figure 39:
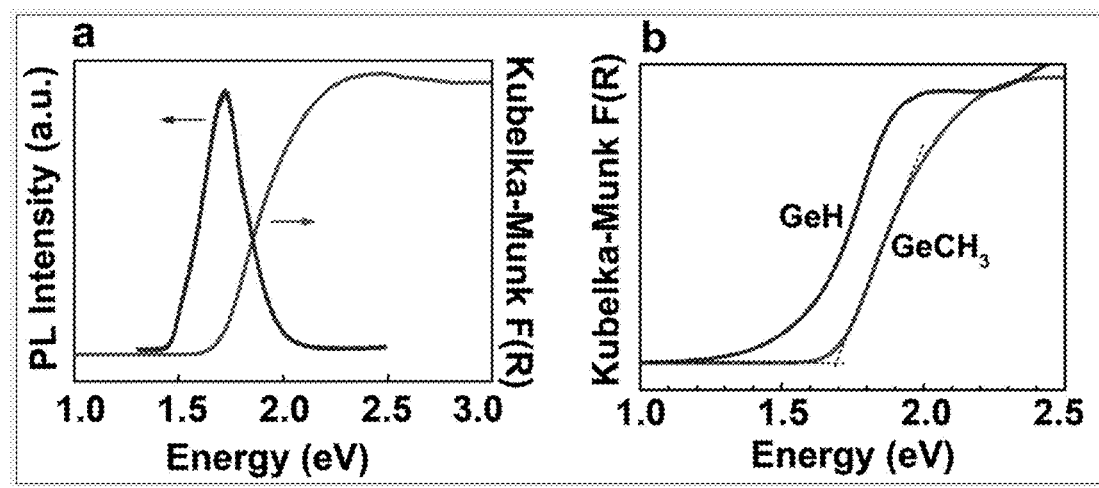
FIG. 39 shows (a) DRA and PL of GeCH$_3$; (b) DRA spectra of GeH (left) and GeCH$_3$ (right) plotted in Kubelka-Munk function versus photon energy.
Figure 40:
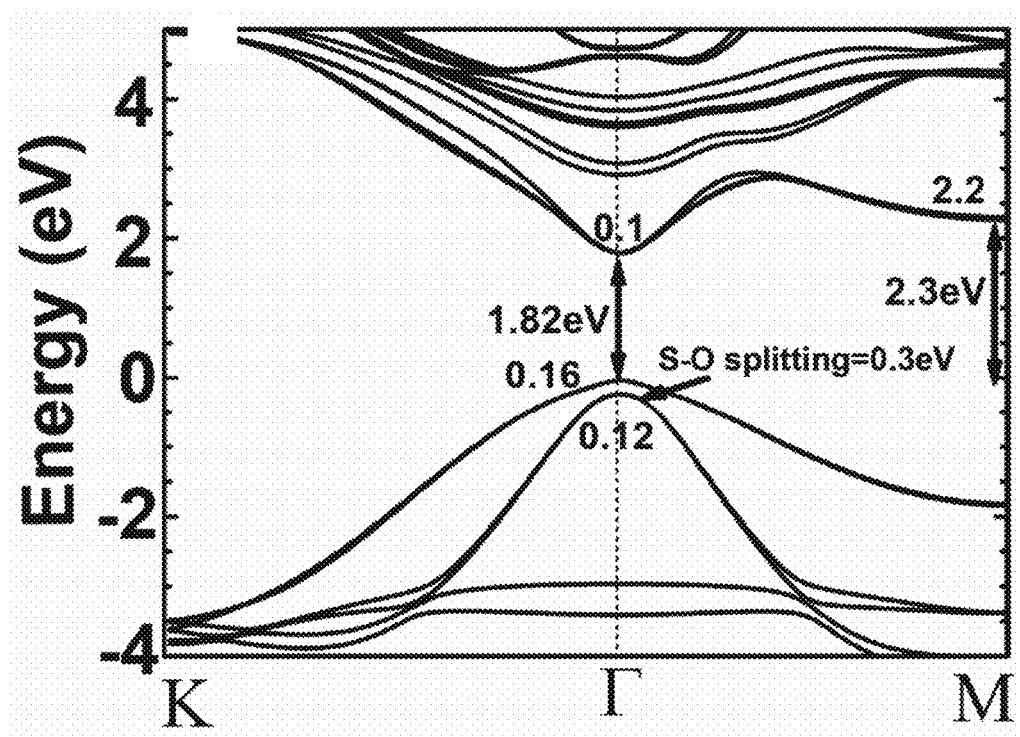
FIG. 40 shows an electronic band structure of a bilayer GeCH$_3$ unit cell calculated using the hybrid HSE06 theory including spin-orbit coupling with experimental lattice parameters (3.96 Å) predicting a 1.82 eV direct band gap.
Figure 41:
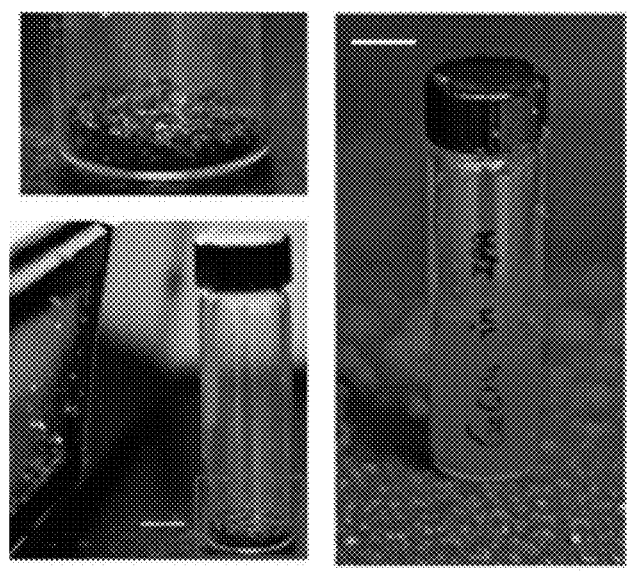
FIG. 41 shows images of GeCH$_3$ photoluminescence of crystals (left) and in suspension in isopropanol (right), upon illumination with a handheld 365 nm light. Scale bars, 1 cm.

The absorption and fluorescence measurements of GeCH$_3$ are consistent with that of a direct band gap semiconductor. GeCH$_3$ has strong photoluminescence (PL) emission centered at 1.7 eV (730 nm (red)), which is similar to the observed diffuse reflectance absorption (DRA) onset at 1.69 eV (FIG. 39a). This corresponds to a 0.1 eV increase in band edge compared to GeH (1.59 eV) (FIG. 39b). Band structure calculations, for the measured structure using the hybrid HSE06 exchange-correlation functional, confirm this band gap, and predict that the 2-layer unit cell has a direct band gap of 1.82 eV (FIG. 40). The red PL can be easily detected by eye under UV illumination in both solid-state samples and in suspension in isopropanol (FIG. 41). The full-width at half maximum (FWHM) of the fluorescence emission is ~250 meV. The absolute quantum yield of the solid flakes was measured to be 0.23%. This represents a minimum bound of the quantum yield, due to the difficulty in correcting for self-absorption in solid-state measurements. The FWHM and quantum yield values are close to those observed in exfoliated single layer MoS2, which are 50-150 meV, and 0.4-0.5%, respectively. Notably, the photoluminescence emission intensity of exfoliated samples is linearly proportional to the number of layers from 13-65 layers (FIG. 30 and FIG. 28-29). The band edge emission does not depend on layer thickness, at least with 13 layers and above, reflecting the relatively weak electronic coupling and orbital overlap of the conduction and valence bands in neighboring layers. The intense PL contrasts with observations of previous reported crystals of GeH, of which negligible band edge PL has been observed. Taken together, the data shows that the nature of the covalently modifiable surface ligand can tune the optoelectronic properties of these materials.

Figure 42:
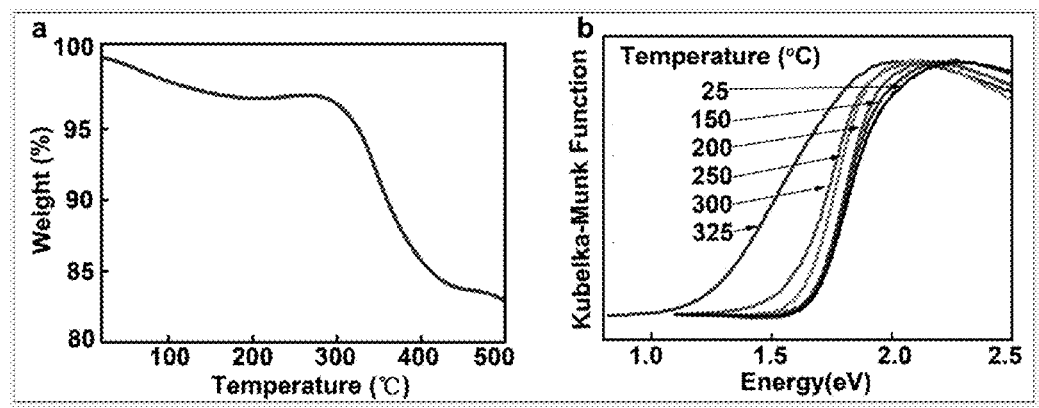
FIG. 42 shows (a) thermogravimetric analysis of GeCH$_3$; and (b) DRA spectra.
Figure 43:
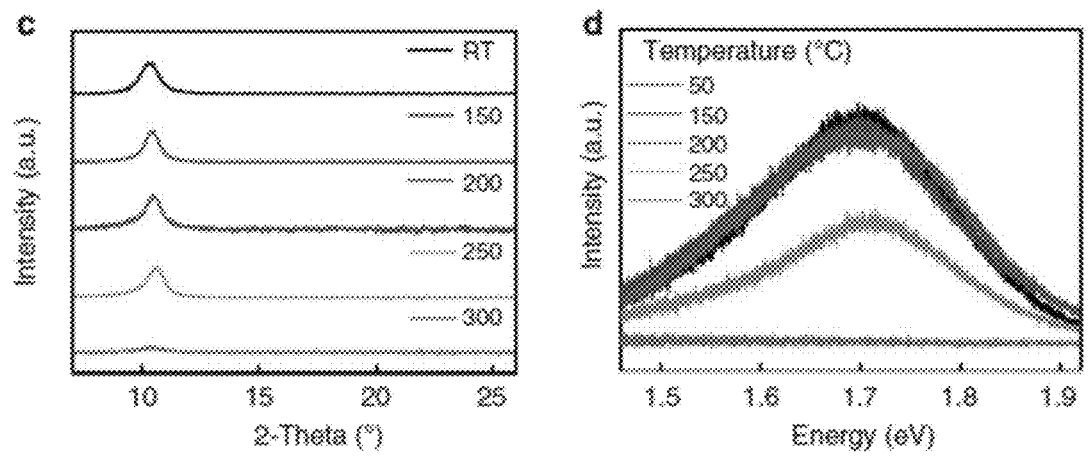
FIG. 43 shows (c) DRA spectra of bulk GeCH$_3$ after annealing in 5% H$_2$/Ar for four hours at various temperatures; and (d) Photoluminescence spectra of a single exfoliated GeCH$_3$ flake using the same annealing procedure.

As discussed above, GeH begins to amorphize upon annealing at 75° C., is completely amorphous above 175° C., and starts to dehydrogenate between 200° C. and 250° C. In contrast, GeCH$_3$ has considerably enhanced thermal stability. According to thermogravimetric analysis, a transition occurs starting at 300° C. (FIG. 42a) that corresponds to the expected mass loss for approximately 90% CH$_3$ termination, which is in excellent agreement with elemental analysis. As detailed above, DRA is a much more sensitive probe of the degree of amorphization than most techniques, due to the reduced band gap of amorphous germanium. There is virtually no shift in band edge emission up to 200° C., whereas after annealing at 250° C. and 300° C., the band edge red-shifts by 0.06 and 0.10 eV, respectively (FIG. 42b). The powder XRD pattern also shows negligible changes after annealing up to 250° C., but it is almost completely amorphous after annealing at 300° C. (FIG. 43c). The intensity of photoluminescence emission also started to decrease after annealing at 250° C. (FIG. 43d). These techniques collectively demonstrate that GeCH$_3$ begins to amorphize at approximately 250° C. Considering the lack of PL in the studies listed above on GeH, the enhanced stability upon methyl termination is likely necessary to realize semiconductor properties, such as band edge photoluminescence, that are often disrupted by defect states.

Example 4. Band Gap Tuning of Germanane with Sn Alloying

Figure 44:
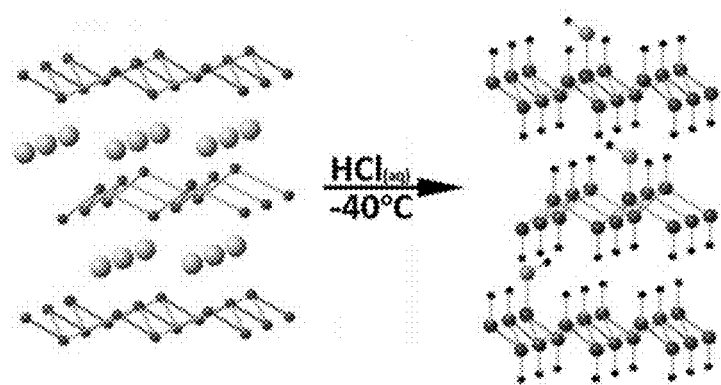
FIG. 44 is a schematic of the topotactic deintercalation of a layered CaGe$_{2-2x}$Sn$_{2x}$ zintl phase.
Figure 45:
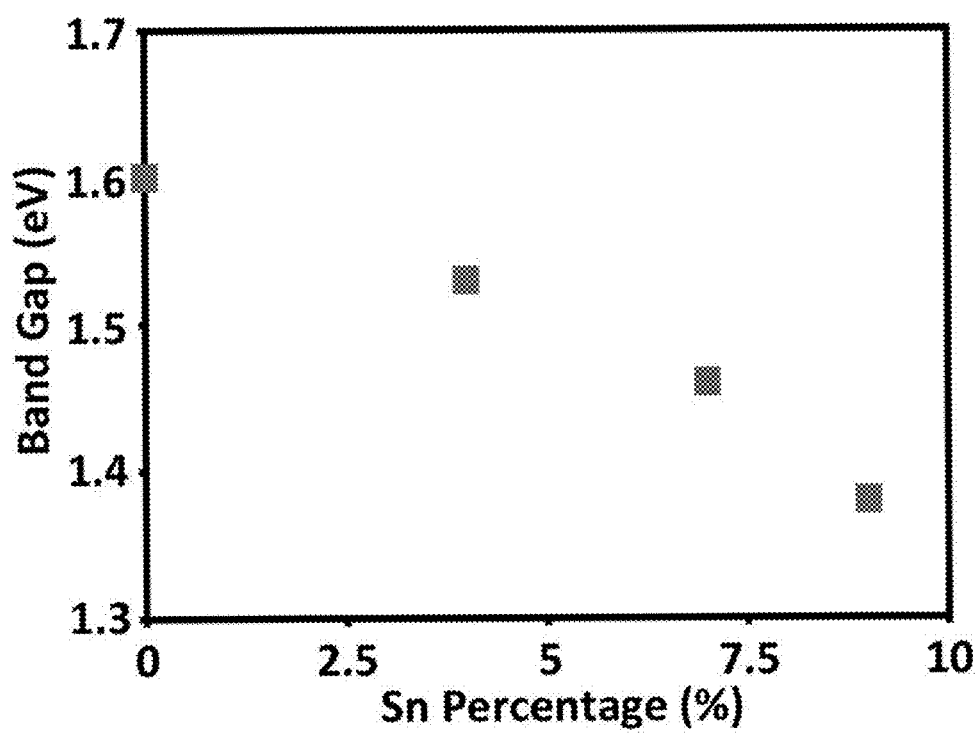
FIG. 45 is an XRD spectra of the CaGe$_{2-y}$Sn$_y$.
Figure 46:
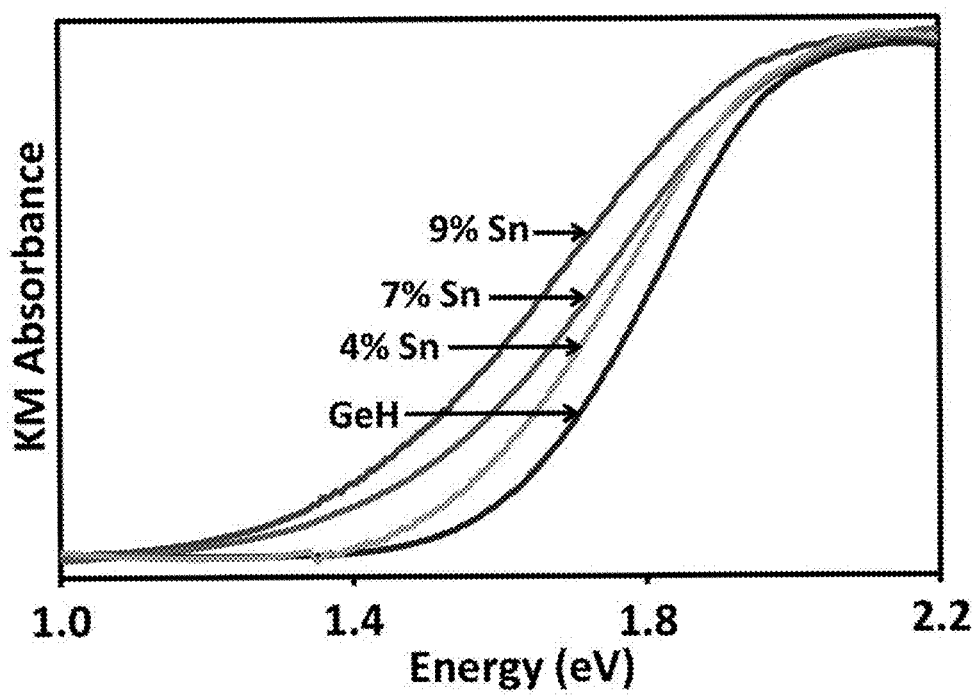
FIG. 46 is an image of the CaGe$_{2-y}$Sn$_y$.
Figure 47:
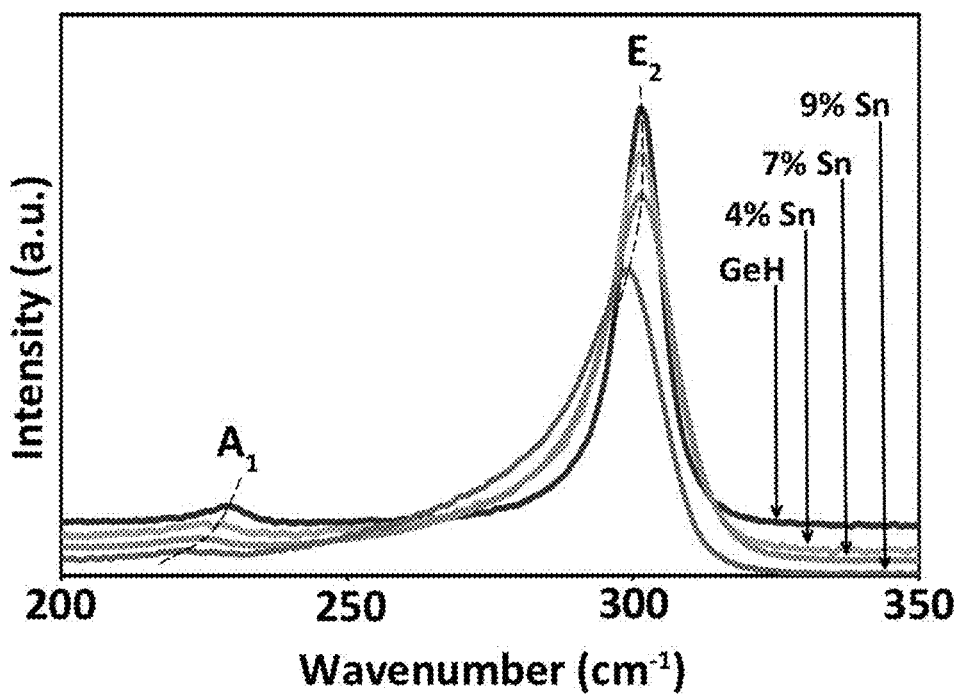
FIGS. 47 & 48 show XRD lattice parameters of the 2D Ge$_x$Sn$_{1-x}$ analogs.
Figure 48:
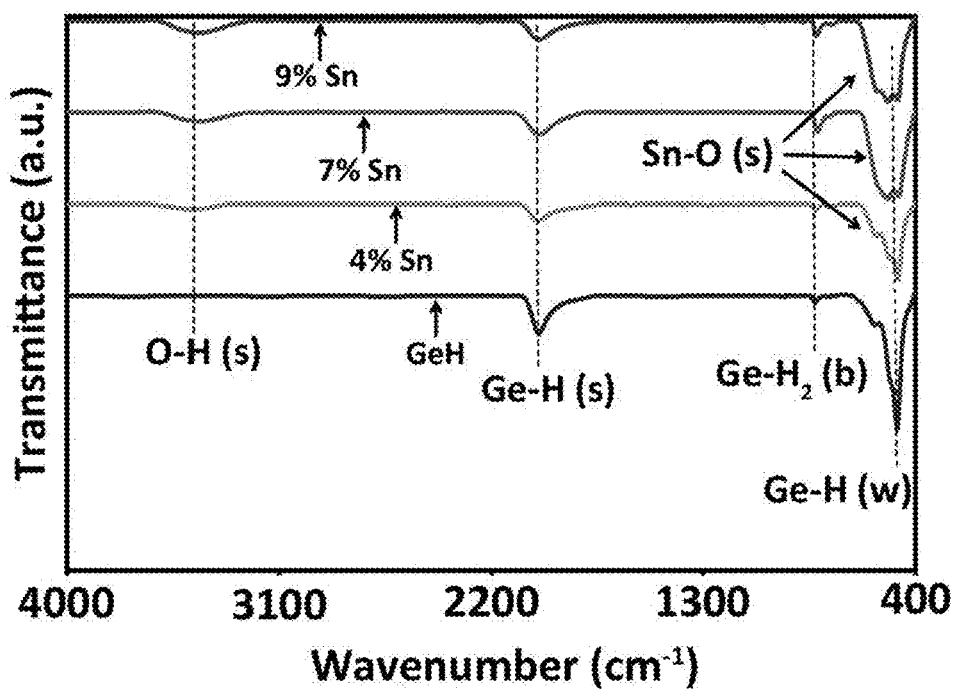

2D Ge$_{1-x}$Sn$_{xH1-xOHx}$ analogues were created by the topotactic deintercalation of a layered CaGe$_{2-y}$Sn$_y$ Zintl phase in aqueous HCl at −40° C. for 8-10 days (FIG. 44). Crystals of CaGe$_{2-y}$Sn$_y$ were synthesized by sealing stoichiometric amounts of Ca, Ge and Sn inside a quartz tube, annealing to 950-1050° C., and cooling over a period of 3-5 days. X-ray diffraction (XRD) measurements confirmed the successful formation of said Zintl phases. The resulting $CaGe_{2-y}Sn_y$ formed two-layer P63mc unit cells, similar to $\alpha$-$CaGe_2$. A significant increase in both the a-b and the c-lattice parameters confirms the incorporation of Sn in the system (FIGS. 45 & 46). Furthermore, reactions in which the Sn/Ge ratio was increased demonstrates no additional lattice parameter shifts and instead the formation of an impurity tin phase is observed. After HCl treatment, the product was filtered and washed with water to remove residual $CaCl_2$, then acetonitrile, and subsequently dried under vacuum. The resulting platelet-shaped crystallites are 2-3 mm in length and width, and 10-100 μm in thickness (FIG. 46). XRD of these platelets confirmed the transformation into a 2D $Ge_xSn_{1-x}$ analog. Compared to the original $CaGe_{2-y}Sn_y$ unit cell parameters, the 2D $Ge_{1-x}Sn_x$ (FIG. 47) is slightly contracted in the a and b direction and are significantly expanded in the c-direction (FIG. 48). After deintercalation there is still an increase in all the unit cell parameters with increasing Sn, suggesting that Sn remains in the lattice. The observed ~0.1 Å contraction in the a and b direction is consistent with the change observed for going from $CaGe_2$ to GeH. However, the observed 1.2 Å c-axis expansion is much larger than the ~0.4 Å increase that is observed when replacing a $Ca^{2+}$ in $CaGe_2$ with 2 Ge—H bonds between each layer. This suggests the presence of —OH termination of the Sn substituents.

Figure 49:
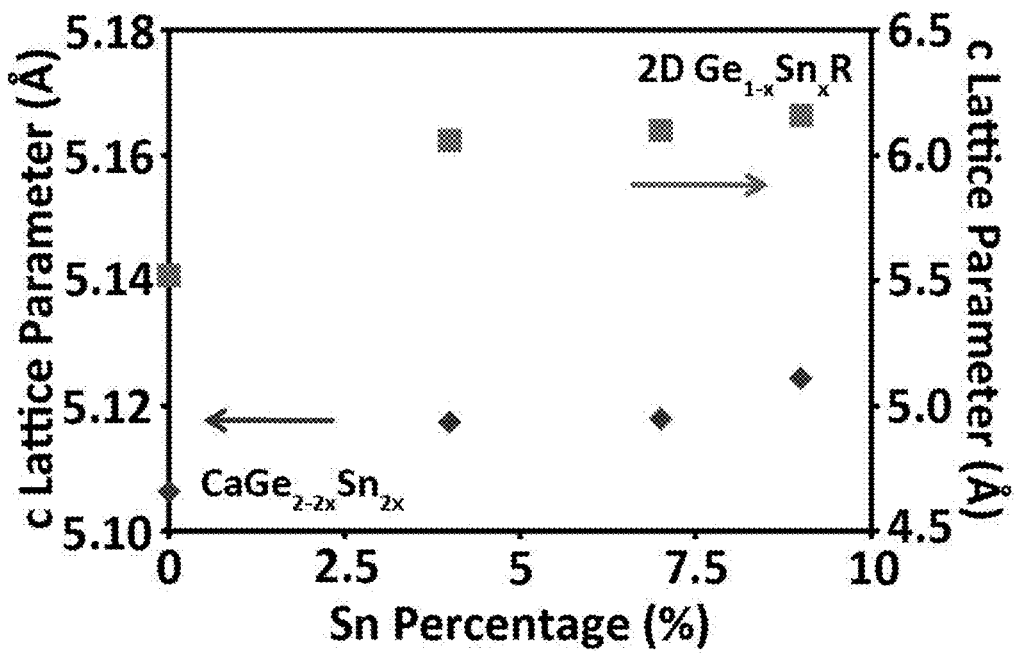
FIG. 49 shows FTIR analysis of the 2D Ge$_x$Sn$_{1-x}$ samples.

To further elucidate the identity of the surface terminating ligand, transmission-mode Fourier Transform Infrared Spectrosocopy (FTIR) measurements were performed on the 2D Ge1-xSnx samples (FIG. 49). With increasing Sn concentration, there is an emergence of a broad O—H stretching mode at ~3450 $cm^{-1}$, as well as a broad, intense Sn—O stretching mode centered at ~560 $cm^{-1}$, which is consistent with previously reported assignments. The emergence of Sn—H stretching modes centered at ~1700-1800 $cm^{-1}$ is not observed with increasing Sn. Additionally, in all samples, it is observed that extremely strong Ge—H stretching modes are centered at ~2000 $cm^{-1}$, weaker wagging modes occur at 570 $cm^{-1}$, 507 $cm^{-1}$, and 475 $cm^{-1}$, and weak vibrational modes occur at 770 and 825 $cm^{-1}$, consistent with bond-bending Ge—H2 from nearest neighbor Ge atoms at the edges of the crystalline sheets. There is no observation of the broad intense, Ge—O—Ge or Ge—O vibrational modes that occur between 800 and 1000 $cm^{-1}$. Furthermore, there is a consistent redshift in the Ge—H stretching frequency and a major Ge—H wagging mode, upon increasing Sn incorporation. For example, at 9% Sn, the Ge—H stretching frequency decreases from 2002 $cm^{-1}$ to 1988 $cm^{-1}$, and the major Ge—H wagging mode decreases from 482 $cm^{-1}$ to 470 $cm^{-1}$. Therefore, after deintercalation in HCl, the Sn atoms are terminated with —OH groups, and the Ge atoms remain terminated with —H.

Figure 50:
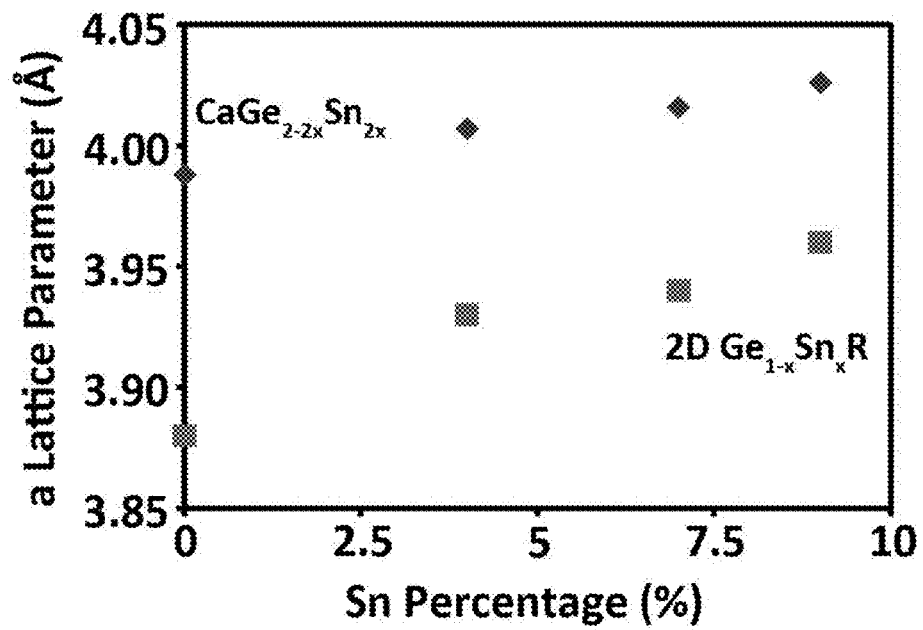
FIG. 50 shows Raman spectroscopy analysis of the 2D Ge$_x$Sn$_{1-x}$ samples.

Raman spectroscopy further confirms the alloy formation of the 2D network. Crystalline GeH as an E2 Ge—Ge stretching mode at 302 $cm^{-1}$ and an A1 vibration at 228 $cm^{-1}$. With increasing Sn, there is an increasing shift in both vibrations to lower energies, and at 9% Sn, the E2, and A1 mode shift to 299 $cm^{-1}$ and 221 $cm^{-1}$, respectively (FIG. 50). The full-width-half maximum (FWHM) of the E2 vibration also increases with increasing Sn concentration. The decrease in energy, as well as the increased FWHM, is consistent with the expected Raman shifts with increasing tin due to the increasing average Ge—Ge/Sn bond length, as well as the increased disorder in the mass distribution.

Figure 51:
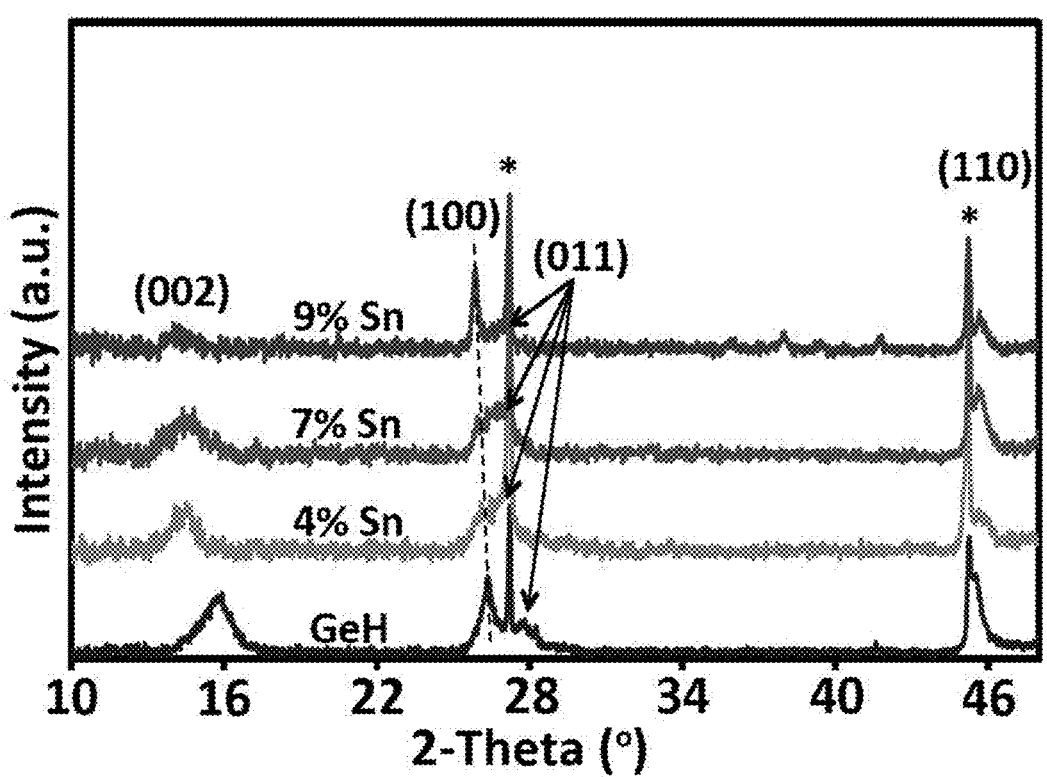
FIG. 51 shows diffuse Reflectance Absorption measurements of the 2D Ge$_x$Sn$_{1-x}$ samples.

To determine the influence of Sn—OH substitutions on the optical band gap of GeH, diffuse Reflectance Absorption measurements was performed on powders (FIG. 51a). The silver-black materials have a broad absorption over all visible wavelengths, and there is a systematic decrease in the absorption band edge, as well as the absorption maximum with increasing tin concentration (FIG. 51b). A linear approximation of the absorption edge suggests a decrease in the band edge from 1.59 eV for GeH, down to 1.38 eV for 9% Sn.

Various features and advantages of the invention are set forth in the following claims.

What is claimed is:

1. A two-dimensional layer comprising M-R, wherein M is selected from the group consisting of Ge, and Sn; wherein R is $C_{1-18}$ alkyl; and wherein the M-R is crystalline.
2. The two-dimensional layer of claim 1, wherein M is Ge.
3. The two-dimensional layer of claim 1, wherein R is $CH_3$.
4. The two-dimensional layer of claim 1, wherein the layer is stable up to about 300° C.
5. The two-dimensional layer of claim 1, wherein the layer has a band gap of from about 0.1 eV to about 3.4 eV.
6. A stack comprising the two-dimensional layer of claim 1.
7. The stack of claim 6, wherein M is Ge.
8. The stack of claim 6, wherein R is $CH_3$.
9. A two-dimensional layer of claim 1, wherein M-R is $Ge(CH_3)$.
10. A stack comprising the two-dimensional layer of claim 9.
11. The two-dimensional layer of claim 1, wherein R is a branched or unbranched hydrocarbon.
12. A light-emitting device comprising the two-dimensional layer of claim 1.
13. The light-emitting device of claim 12, wherein the light-emitting device is selected from the group consisting of light-emitting diodes and lasers.
14. The light-emitting device of claim 12, wherein the two dimensional layer comprises $GeCH_3$.
15. A light-absorbing device comprising the two dimensional layer of claim 1.
16. The light-absorbing device of claim 15, wherein the light-absorbing device is selected from the group consisting of photovoltaics and photodetectors.
17. The light-absorbing device of claim 15, wherein the two dimensional layer comprises $GeCH_3$.
18. A transistor comprising the two-dimensional layer of claim 1.
19. The transistor of claim 18, wherein the two dimensional layer comprises $GeCH_3$.

* * * * *